United States Patent
Smith

(10) Patent No.: US 11,235,200 B2
(45) Date of Patent: Feb. 1, 2022

(54) CRITICAL POWER ADAPTIVE TRAINING WITH VARYING PARAMETERS

(71) Applicant: Nautilus, Inc., Vancouver, WA (US)

(72) Inventor: Joshua S. Smith, Portland, OR (US)

(73) Assignee: Nautilus, Inc., Vancouver, WA (US)

( * ) Notice: Subject to any disclaimer, the term of this patent is extended or adjusted under 35 U.S.C. 154(b) by 192 days.

(21) Appl. No.: 16/794,151

(22) Filed: Feb. 18, 2020

(65) Prior Publication Data

US 2020/0179754 A1 Jun. 11, 2020

Related U.S. Application Data

(63) Continuation of application No. 16/192,733, filed on Nov. 15, 2018, now Pat. No. 10,603,543.

(Continued)

(51) Int. Cl.
  *G16H 40/63* (2018.01)
  *G16H 20/30* (2018.01)
  (Continued)

(52) U.S. Cl.
  CPC ...... *A63B 24/0006* (2013.01); *A63B 24/0075* (2013.01); *A63B 24/0087* (2013.01);
  (Continued)

(58) Field of Classification Search
  CPC ............ A63B 24/0006; A63B 24/0075; A63B 71/0622; A63B 24/0087; A63B 22/0023;
  (Continued)

(56) References Cited

U.S. PATENT DOCUMENTS 10,603,543 B2   3/2020 Smith
10,688,345 B1 * 6/2020 Lynch ................ A63B 23/1281
  (Continued)

FOREIGN PATENT DOCUMENTS

EP      1993681 A1    11/2008

OTHER PUBLICATIONS

International Searching Authority, International Search Report and Written Opinion, PCT Patent Application PCT/US2018/065233, dated Apr. 12, 2019, 13 pages.

(Continued)

*Primary Examiner* — Sundhara M Ganesan
(74) *Attorney, Agent, or Firm* — Perkins Coie LLP

(57) ABSTRACT

An adaptive training system can determine a finite work capacity and critical power and use those determinations to generate an adaptive training programs for workout parameters. To determining a finite work capacity and critical power, the adaptive training system can receive workout data; generate data points by determining, for each workout, a maximum amount of work done for each of multiple time window sizes; fit these workout data points to a function; and determine a critical power and finite work capacity based on the fitted function. Once the adaptive training system has determined a critical power and finite work capacity, the adaptive training system can use them to generate an adaptive training program by keeping a function defined by a set of workout parameters below an ability function that is based on the critical power and finite work capacity.

20 Claims, 16 Drawing Sheets

Related U.S. Application Data

(60) Provisional application No. 62/609,298, filed on Dec. 21, 2017.

(51) Int. Cl.
  *G16H 40/67* (2018.01)
  *A63B 24/00* (2006.01)
  *A63B 71/06* (2006.01)

(52) U.S. Cl.
  CPC ......... *A63B 71/0622* (2013.01); *G16H 20/30* (2018.01); *G16H 40/63* (2018.01); *G16H 40/67* (2018.01)

(58) Field of Classification Search
  CPC ............ A63B 22/0605; A63B 22/0235; A63B 24/0062; A63B 71/0619; A63B 2225/50; A63B 2230/01; A63B 2225/105; A63B 2220/18; A63B 2220/17; A63B 2071/0625; A63B 2220/836; A63B 2220/30; A63B 2220/833; A63B 2071/065; A63B 2024/0068; A63B 2230/75; A63B 2071/0675; A63B 2225/20; A63B 2071/0655; A63B 2220/807; A63B 2220/808; A63B 2220/806; A63B 2220/20; A63B 2220/40; A63B 2024/0093; A63B 2220/80; A63B 2024/0012; G09B 19/0038; G16H 40/63; G16H 20/30; G16H 40/67; G16H 50/30

See application file for complete search history.

(56) References Cited

U.S. PATENT DOCUMENTS

| | | |
|---|---|---|
| 2009/0069156 A1 | 3/2009 | Kurunmaeki et al. |
| 2016/0345891 A1 | 12/2016 | Kirby et al. |
| 2017/0100637 A1 | 4/2017 | Princen et al. |
| 2019/0192906 A1 | 6/2019 | Smith |
| 2020/0016453 A1 | 1/2020 | Kollreider et al. |

OTHER PUBLICATIONS

International Searching Authority, International Search Report and Written Opinion, PCT Patent Application PCT/US2021/016941, dated May 25, 2021, 15 pages.

\* cited by examiner

CRITICAL POWER ADAPTIVE TRAINING WITH VARYING PARAMETERS

BACKGROUND

Millions of people desire to train and get in better shape. For many, this is difficult due to lack of time or the effort involved. Many systems have been developed to help people begin training or maximize their training efforts. For example, people read fitness magazines, follow workout programs, attend classes, hire personal trainers, etc. While some of these programs are tailored to individuals, they often fail to maximize a person's potential or cause frustration due to overwork. One cause of this is that many of these programs are not based on measures of a person's potential to perform exercise. Even for programs that uses some previous method to tailor programs to an individual, these methods has been difficult to implement and results have been inaccurate. Furthermore, training programs developed based on these measurements have failed provide correct levels of intensity and duration.

For example, VO2 is a measurement system that determines a maximum amount of oxygen a person can use. VO2 is measured by dividing an amount of oxygen inhaled per minute by an amount of oxygen exhaled per minute. Thus, VO2 based assessments require a user to be attached to an apparatus that can measure air intake and output and an amount of oxygen in the air. Furthermore, VO2 measurements are generally static for an individual and there is no clear way to translate a VO2 measurement into a duration or intensity level for training. Some techniques have been developed to provide workout guidelines based on heart rate measurements. However, these still require a specialized heart rate monitor attached to a person, are inaccurate, and do not correctly estimated limits on time or intensity training metrics.

SUMMARY

The present technology provides an adaptive training system and related methods that overcome drawbacks of the prior art and provide other benefits. In at least one embodiment, an adaptive training system can generate training programs adapted to a particular user based on critical power and varying workout parameters. A person's power output is equal to their indefinite ability produce power ("critical power") in combination with some finite capacity to work above their critical power ("finite work capacity") over a given amount of time. A practical application of a user's critical power and finite work capacity is using them to generate a user specific training program. A training program can be a single training session or series of training sessions with specified parameters based on a critical power or finite work capacity determination for a user. Training programs based on critical power are accurate, require no special heart rate or oxygen measurement devices, and are adaptable to a user's changing ability level. Furthermore, the transformations of critical power to a training program can be provided for various types of exercises and timeframes.

The adaptive training system of one or more embodiments includes two aspects of applying the critical power analysis: (1) determining a specific user's finite work capacity and critical power without requiring heart rate information or use of an invasive measurement apparatus, and (2) using those determinations to generate adaptive training programs, specific for the user, for any given set of workout parameters. In determining a user's finite work capacity and critical power, the adaptive training system can receive statistics from one or more of the user's current or prior workouts or segments of a workout, and determine the user's finite work capacity and critical power based only on time intervals and measurements indicative of power output (e.g. running speed, watts of stationary bike output, repetitions performed over a time, etc.). Furthermore, as a user logs additional workouts, these finite work capacity and critical power determinations can be updated, and new or modified training programs can be generated for the user. In some implementations, more recent workouts can have a greater weight in determining these measurements as compared to older workout statistics. For example, a scalar decay function can be applied to workout data to weight it based on age.

The adaptive training system can determine a finite work capacity and critical power for a particular user by generating data points from one or more workout statistic sets. Each data point can be a measure of the user's maximum work performed in a workout for any time window of a particular length. For a particular workout, multiple data points can be taken using different time window lengths. Each data point can be a work value computed by taking the maximum integration, for a given time window size, of a function that provides power based on time. Thus, a work data point will be the largest area under the power function for any interval matching the time window size of that data point. Where multiple workouts are used, a final workout statistic set can keep only the largest work value for each time window size from the multiple workouts. The adaptive training system can fit points from one or more workout statistic sets to an ability function. The ability function can be used to determine a critical power, which corresponds to the slope of the ability function, and the finite work capacity, which corresponds to the y-intercept of the ability function. Alternatively, the adaptive training system can use the demonstrated work points in a final workout statistic set as boundary points for future training programs. Additional details regarding determining a users ability function and/or finite work capacity and critical power are discussed below in relation to FIGS. 3-5.

Once the adaptive training system has determined a critical power and finite work capacity, the adaptive training system can use those determinations to generate an adaptive training program for a given set of workout parameters. For any particular workout type, a number of parameters can describe the workout in terms of work and time. For example, in an interval workout with regular intervals, the workout can be defined in terms of five parameters: number of intervals, interval duration, power output during intervals, rest duration, power output during rests. All but one of these parameters can be specified either by a user or based on characteristics of the workout. For example, for a workout on a treadmill, a user can specify interval duration and rest duration, and a power output during the intervals and power output during rests can be determined based on the treadmill settings, such as speed and angle. The adaptive training system can then compute the final parameter, based on the users critical power and finite work capacity, such that a user-specific workout plan can be generated that directs the user's exercise to approach but not pass an exhaustion threshold. For example, the number of intervals can be set such that a function, describing the workout, based on the five parameters mapped in terms of work/time, does not exceed a user's ability function. In various implementations, the ability function can be provided by the user's work capacity. In some implementations, the ability function can be a linear or non-linear function fit to a workout statistic set, as discussed above. The slope of the ability function can define the user's critical power and the y-intercept can define the user's finite work capacity. In some implementations, once a critical power (CP) and finite work capacity (W') have been determined, the ability function can be modified to account for real-world circumstances, such as the fact that given zero time a user's ability to perform work is also zero. This modification can include turning the ability function into a combined linear and logarithmic function. For example, the ability function can be specified as $W=+W'*\log(t+1)$, where W is a work ability (dependent variable) and t is a given amount of time (independent variable). In some implementations, the ability function can be the workout statistic set used as a boundary for corresponding points of training programs. Additional details regarding using an ability function or critical power and finite work capacity to generate a specific training program for a workout type defined by parameters are discussed below in relation to FIGS. 6 and 7.

In various implementations, the adaptive training system can be implemented, at least in part, as an integrated component of a workout machine, in a network of workout machines that share information, as an "app," in a fitness tracker, as part of a server-based information system (e.g. accessed through a webpage), or any combination thereof. For example, the adaptive training system can be integrated into a workout machine instrumented to take work measurements indicative of power output (e.g. resistance and revolutions per minute, time and distance, etc.). The adaptive training system can use these measurements to determine work vs. time data points. These data points can be used to compute critical power and finite work capacity of the user (e.g. by fitting them to an ability function). The adaptive training system can then provide a training program configured to bring the user within a threshold amount of, but not surpass, an exhaustion point determined based on the critical power and finite work capacity or ability function. The training program can be provided as visual output with suggested workout parameters. Alternatively or in addition, the training program can be provided as automatic adjustments to workout settings (e.g. treadmill speed). An example of this configuration is described below in relation to FIG. 8A.

As another example, the adaptive training system can be implemented in a network of workout machines. In this example, the adaptive training system can identify the user based on authentication data provided to a workout machine or through a mobile device, such as through a website or app, by scanning a QR code on the machine, etc. Then, during a subsequent workout, data points from measurements on that machine can be added to data points from measurements previously taken on other machines to maintain updated critical power and finite work capacity or ability function gauges. These can be used to generate a training program. The training program can include workout suggestions, which can be provided on the networked machine or on the mobile device. Alternatively or in addition, the training program can include workout machine settings, which the adaptive training system can automatically apply on the machine. An example of this configuration is described below in relation to FIG. 8B.

As yet a further example, the adaptive training system can be implemented on a mobile device or other computing system, e.g. as an app, through a webpage, or as a function of a smartwatch or other fitness device. In some implementations, the adaptive training system can automatically gather data (e.g. distance, amount of time, speed, elevation change, etc.) or a user can manually enter it (e.g. by entering distance and time following a run). The adaptive training system can then provide a training program. In some implementations, the training program can include showing further statistics, such as changes in critical power or finite work capacity over time. In some implementations, the training program can provide a suggested workout plan. The suggested workout plan can set aspects of the training program to meet user goals. In some implementations, the training program can include guided workouts or other training suggestions or instructions based on the ability function or critical power and finite work capacity. An example of this configuration is described below in relation to FIG. 8C.

The current technology provides a number of benefits over the prior art. For example, the adaptive training system can determine a critical power and finite work capacity without the need for an heart rate monitor, oxygen equipment, or other invasive equipment attached to a user. In addition, training programs based on critical power or finite work capacity provide a basis for workout levels while not being subject to the inaccuracies from which heart rate monitoring methods suffer. Further, the adaptive training system can be implemented using low power, low processing speed equipment and only needs to store the "best record" data, effectively reducing the amount of required storage capacity, as compared to prior art systems that require large amounts of interrelated data to make a training suggestion.

In various implementations, the adaptive training technology can be implemented as a method, system, or computer-readable storage medium. A workout machine system for automatically providing an adaptive training program can include a workout apparatus that implements a training session of a particular type, with given parameters. The workout machine system can also include an instrument system, integrated with the workout apparatus, that obtains measurements indicative of power output. The workout machine system can also comprise a processing component configured to generate an adaptive training program.

Where the adaptive training technology is implemented as a method it can include various operations and where the adaptive training technology is implemented as a system or computer-readable storage medium a processing component of the system or operating on the computer-readable storage medium can perform the various operations. These operations can comprise: identifying a work value for each particular window size, of multiple window size durations of the measurements indicative of power output. This can be accomplished by identifying a largest integration, of a function specified by the measurements indicative of power output, for an interval matching the particular window size. The operations can also include fitting, as an ability function, a function to the work values identified for the multiple window size durations. The operations can further comprise computing a value for at least one previously unspecified parameter for a training session, such that values of a workout function, that uses the previously unspecified parameter, do not exceed corresponding values of the ability function for any time during a duration for the training session. The operations can also comprise using the at least one previously unspecified parameter to generate the adaptive training program. The adaptive training technology can provide output or automatic workout settings based on the adaptive training program.

In some implementations, the adaptive training technology can include or implement operations comprising obtaining given parameters for a training session and obtaining measurements indicative of power output. The operations can further comprise generating the adaptive training program by: determining, based on the measurements indicative of power output, an ability function or critical power assessment. Generating the adaptive training can further include using (A) the ability function or critical power assessment and (B) the given parameters, to generate the training program. The training program can include a value for at least one previously unspecified parameter. The operations can include providing this adaptive training program.

In various implementations, the adaptive training technology can obtain the measurements indicative of power output through manual entry by a user, through recorded workout statistics taken by a wearable fitness tracker, or through an instrument system integrated into a workout apparatus.

In various implementations, the adaptive training technology can be implemented by a server system connected to multiple workout machines, by one or more workout machines, or by a mobile device associated with a user of a workout apparatus.

In various implementations, the adaptive training technology can be implemented in relation to multiple workout machines connected via a network. The measurements indicative of power output can be taken from a first of the networked workout machines while a second set of measurements indicative of power output can be taken from a second of the networked workout machines. This second set of measurements indicative of power output can be transformed into additional work values for corresponding window sizes and can be weighted based on an age of the second set of measurements. When the adaptive training technology performs the fitting of the function to the work values identified for the multiple window size durations, it can further accomplish this by fitting the function to the additional work values. In some implementations, this fitting can include selecting, for each particular window size, the largest value, of the work values and to the additional work values, corresponding to that particular window size; and fitting the function to the selected largest values for the window sizes.

In some implementations, the adaptive training technology can generate the adaptive training program in response to an identification comprising a code indicative of a user or of a workout apparatus. The identification can be supplied: by the user, by a mobile device associated with the user, or by the workout apparatus. In some implementations, the code indicative of the workout apparatus can be supplied to the mobile device through an image capture system on the mobile device that captures an alphanumeric code, a bar code, or QR code displayed in conjunction with the workout apparatus.

The output or automatic workout settings that the adaptive training technology provides can be output to a server system comprising an indication of an additional determined parameter. Alternatively, the output can be provided to a mobile device comprising an indication of at least one previously unspecified parameter. In some implementations, the output can be to a mobile device comprising data to be operated on by the execution of instructions on the mobile device. This execution can provide a display for a user to implement the adaptive training program. In some implementations, the output can be to a workout apparatus configured to cause a display of the workout apparatus to provide instructions based on the adaptive training program. The output can also include automatic workout settings that cause a workout apparatus to automatically implement the adaptive training program. In some implementations, the output can be provided to a server system or a mobile device and the output is stored in association with a user profile. The user profile can include various information such as: the identified work values, the ability function, statistics of the adaptive training program, measures of actual performance during the training session, biographic specifics, or any combination thereof.

In some implementations, the adaptive training technology can provide an internet-based interface that is accessible through a web browser or mobile device application. The internet-based interface can provide access to a user profile associated with multiple workouts performed by a user.

In various implementations, the measurements indicative of power output can comprise one or more of: speed, revolutions-per-minute, resistance, incline, distance, duration, weight, repetitions, or any combination thereof.

In some implementations, the ability function is a linear function.

In some implementations, the adaptive training technology can be implemented by a server system that obtains additional work values, stored in association with a user profile for the user, and generates the adaptive training program, both of which may be in response to an authentication of the user.

In some implementations, the workout function can be defined for an interval or skip interval type workout. Parameters for the workout function for an interval workout can include the number of intervals, interval duration, power output during intervals, rest duration, power output during rests, or any combination thereof. Parameters for the workout function for a skip interval workout can include the number of intervals, duration of peak work during interval, duration of short rest time within an interval, power output during interval peak, rest duration between intervals, power output during rests, or any combination thereof.

In some implementations, computing the value for the at least one previously unspecified parameter can comprise: obtaining the workout function, from a set of pre-defined functions, based on an indicated workout type for the adaptive training program. The operations can then fill in one or more given parameters in the workout function and solving for the at least one previously unspecified parameter. In some implementations, generating the adaptive training program can comprise selecting data to display as instructions to a user to perform a workout based on at least one previously unspecified parameter. The adaptive training program can also specify the output or automatic workout settings based on the at least one previously unspecified parameter. In some implementations, filling in parameters in the pre-defined function can comprise using one or more default values.

In some implementations, while the user is performing the adaptive training program, the adaptive training technology can also receive further measurements indicative of power output as the adaptive training program is performed. The adaptive training technology can identify further work values based on the further measurements indicative of power output. The adaptive training technology can then update the ability function to further fit the further work values; update one or more parameters of the workout function based on a comparison of the workout function to the updated ability function; generate an updated adaptive training program based on the updated parameters; and update the output or automatic workout settings based on the updated adaptive training program.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

DETAILED DESCRIPTION

Figure 1:
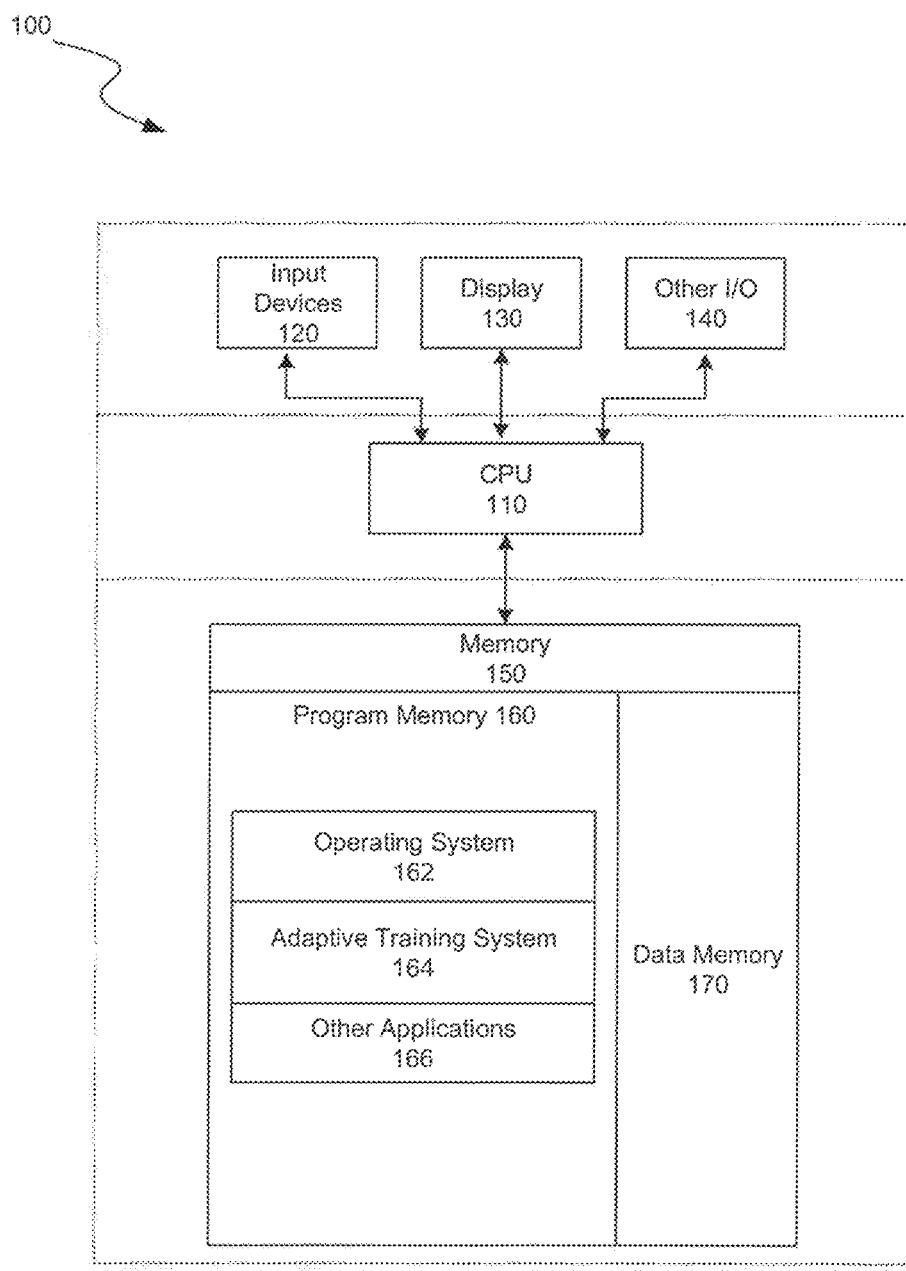
FIG. 1 is a block diagram illustrating an overview of devices on which some implementations can operate.

Turning now to the figures, FIG. 1 is a block diagram illustrating an overview of devices on which some implementations of the disclosed technology can operate. The devices can comprise hardware components of a device 100 that can assess critical power and use the assessment to generate an adaptive training program. Device 100 can include one or more input devices 120 that provide input to the CPU(s) (processor) 110 notifying it of events. The events can be mediated by a hardware controller that interprets the signals received from the input device and communicates the information to the CPU 110 using a communication protocol. Input devices 120 include, for example, instrumentation on workout equipment that measures values indicative of power output (e.g. number of rotations, speed, incline, resistance, etc.), an accelerometer, a pedometer, a touchscreen, an infrared sensor, a wearable input device, a camera- or image-based input device, a microphone, a mouse, a keyboard, or other user input devices.

CPU 110 can be a single processing unit or multiple processing units in a device or distributed across multiple devices. CPU 110 can be coupled to other hardware devices, for example, with the use of a bus, such as a PCI bus or SCSI bus. The CPU 110 can communicate with a hardware controller for devices, such as for controlling settings of a workout machine or providing output to a display 130. Display 130 can be used to display text or graphics. In various implementations, display 130 provides a training program as features of a suggested workout on a workout machine display, on a phone display, on a fitness device display, or through a computer monitor display. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other input/output ("I/O") devices 140 can also be coupled to the processor, such as a network card, video card, audio card, USB, firewire or other external device, camera, printer, speakers, CD-ROM drive, DVD drive, disk drive, or Blu-Ray device. In some implementations, other I/O can include a haptic feedback system, such as vibrations through a mobile device or fitness device that can provide indications of a training program. In some implementations, other I/O can include a connection, either directly or across a network, that provides for automatic controls and settings to be provided to workout machines based on a determined training program.

In some implementations, the device 100 also includes a communication device capable of communicating wirelessly or wire-based with a network node. The communication device can communicate with another device or a server through a network using, for example, TCP/IP protocols. Device 100 can utilize the communication device to distribute operations across multiple network devices.

The CPU 110 can have access to a memory 150 in a device or distributed across multiple devices. A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 150 can include program memory 160 that stores programs and software, such as an operating system 162, adaptive training system 164, and other application programs 166. Memory 150 can also include data memory 170 that can include power measurements, windowing data points, critical power or finite work capacity determinations, parameterized transformations for various workouts in terms of work, adaptive workout programs based on ability functions, configuration data, settings, user options or preferences, etc., which can be provided to the program memory 160 or any element of the device 100.

Some implementations can be operational with numerous other computing system environments or configurations. Examples of computing systems, environments, or configurations that may be suitable for use with the technology include, but are not limited to, workout machines, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2:
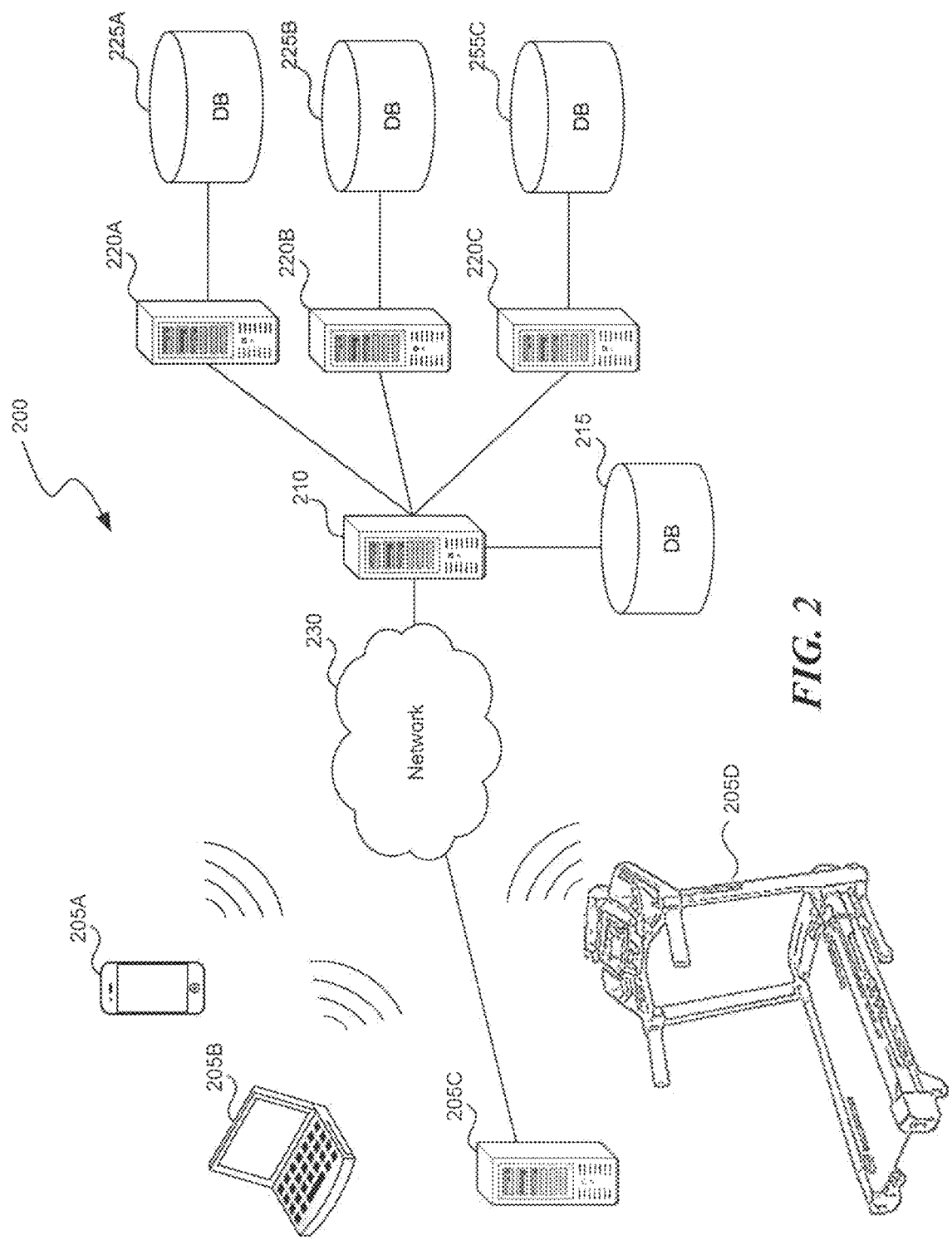
FIG. 2 is a block diagram illustrating an overview of an environment in which some implementations can operate.

FIG. 2 is a block diagram illustrating an overview of an environment 200 in which some implementations of the disclosed technology can operate. Environment 200 can include one or more computing enabled devices 205A-D, examples of which can include device 100. For example, computing enabled devices can include any of a mobile phone or wearable device 205A, laptop 205B, desktop or server 205C, or exercise equipment 205D, which can be stand alone or networked and configured to collect workout data. Computing enabled devices 205 can operate in a networked environment using logical connections 210 through network 230 to one or more remote computers, such as a server computing device.

In some implementations, server 210 can be an edge server which receives client requests and coordinates fulfillment of those requests through other servers, such as servers 220A-C. Server computing devices 210 and 220 can comprise computing systems, such as device 100. Though each server computing device 210 and 220 is displayed logically as a single server, server computing devices can each be a distributed computing environment encompassing multiple computing devices located at the same or at geographically disparate physical locations. In some implementations, each server 220 corresponds to a group of servers.

Computing enabled devices 205 and server computing devices 210 and 220 can each act as a server or client to other server/client devices. Server 210 can connect to a database 215. Servers 220A-C can each connect to a corresponding database 225A-C. As discussed above, each server 220 can correspond to a group of servers, and each of these servers can share a database or can have their own database. Databases 215 and 225 can warehouse (e.g. store) information such as previous workout data, user profile data, workout statistics, historical critical power and finite work capacity determinations, etc. Though databases 215 and 225 are displayed logically as single units, databases 215 and 225 can each be a distributed computing environment encompassing multiple computing devices, can be located within their corresponding server, or can be located at the same or at geographically disparate physical locations.

Network 230 can be a local area network (LAN) or a wide area network (WAN), but can also be other wired or wireless networks. Network 230 may be the Internet or some other public or private network. Computing enabled devices 205 can be connected to network 230 through a network interface, such as by wired or wireless communication. While the connections between server 210 and servers 220 are shown as separate connections, these connections can be any kind of local, wide area, wired, or wireless network, including network 230 or a separate public or private network.

Figure 3:
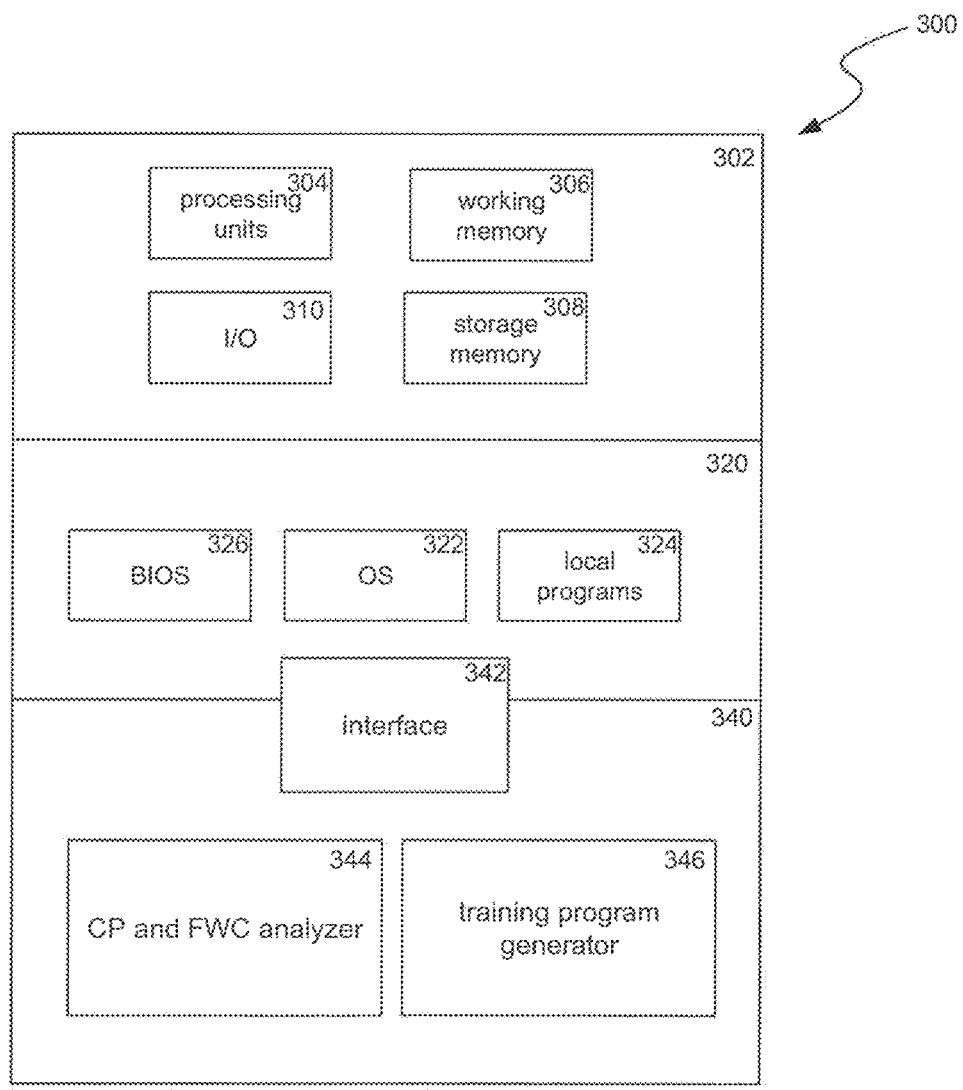
FIG. 3 is a block diagram illustrating components which, in some implementations, can be used in a system employing the disclosed technology.

FIG. 3 is a block diagram illustrating components 300 which, in some implementations, can be used in a system employing the disclosed technology. The components 300 include hardware 302, general software 320, and specialized components 340. As discussed above, a system implementing the disclosed technology can use various hardware including processing units 304 (e.g. CPUs, GPUs, APUs, etc.), working memory 306, storage memory 308 (local storage or as an interface to remote storage, such as storage 215 or 225), and input and output devices 310. In various implementations, storage memory 308 can be one or more of: local devices, interfaces to remote storage devices, or combinations thereof. For example, storage memory 308 can be a set of one or more hard drives (e.g. a redundant array of independent disks (RAID)) accessible through a system bus or can be a cloud storage provider or other network storage accessible via one or more communications networks (e.g. a network accessible storage (NAS) device, such as storage 215 or storage provided through another server 220). Components 300 can be implemented in a computing enabled device such as computing enabled devices 205 or on a server computing device, such as server computing device 210 or 220.

General software 320 can include various applications including an operating system 322, local programs 324, and a basic input output system (BIOS) 326. Specialized components 340 can be subcomponents of a general software application 320, such as local programs 324. Specialized components 340 can include critical power (CP) and finite work capacity (FWC) analyzer 344, training program generator 346, and components which can be used for providing user interfaces, transferring data, and controlling the specialized components, such as interface 342. In some implementations, components 300 can be in a computing system that is distributed across multiple computing devices or can be an interface to a server-based application executing one or more of specialized components 340.

In some implementations, critical power and finite work capacity analyzer 344 can receive power output statistics for a user, e.g. through interface 342, and can use them to determine the user's critical power and finite work capacity. For example, where components 300 are part of a workout machine, I/O 310 can include an instrument system, integrated with the workout machine, that takes measurements indicative of power output. I/O 310 can then use interface 342 to provide the measurements indicative of power output as power output statistics to critical power and finite work capacity analyzer 344. As another example, where components 300 are part of a mobile device, I/O 310 can include a user interface that takes user entered measurements indicative of power output (e.g. run time and distance). I/O 310 can then use interface 342 to provide these as power output statistics to critical power and finite work capacity analyzer 344. In some implementations, critical power and finite work capacity analyzer 344 can determine a critical power and finite work capacity by determining maximum work data points. Each maximum work data point can correspond to a largest area under a graph of the power output statistics for any window of a given size. Each data point can represent an amount of work the user is able to perform in a given timeframe. The critical power and finite work capacity analyzer 344 can then fit a function, in the work range for the time domain, to the highest data points for each window size across workouts. In some implementations, critical power and finite work capacity analyzer 344 can provide this fitted function in place of an explicit critical power or finite work capacity values. In some implementations where the fitted function is linear, the critical power can be the slope of the fitted function and the finite work capacity can be the y-intercept. In some implementations, once a critical power (CP) and finite work capacity (W') have been determined, the ability function can be converted into a combined linear and logarithmic function. For example, the ability function can be specified as $W=CP*t+W'*\log(t+1)$, where W is a work ability (dependent variable) and t is a given amount of time (independent variable). Additional details on determining critical power and finite work capacity from power output statistics are discussed below in relation to FIGS. 4 and 5.

In some implementations, training program generator 346 can generate a user-specific training program with at least one workout when a partial set of workout parameters and a user's critical power and finite work capacity are given. In some implementations, the workout parameters can be received through interface 342, e.g. based on user input, default values, specified goals, etc. The user's critical power and finite work capacity can be determined by critical power and finite work capacity analyzer 344. Training program generator 346 can determine the full set of workout parameters to customize the workout for the particular user by computing the missing parameter that keeps values of a function defining the workout below values of a function defining the user's ability (e.g. the function fit to the data points by critical power and finite work capacity analyzer 344). Additional details on generate a training program with at least one user specific workout based on a critical power and finite work capacity are discussed below in relation to FIGS. 6 and 7.

Those skilled in the art will appreciate that the components illustrated in FIGS. 1-3 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 4:
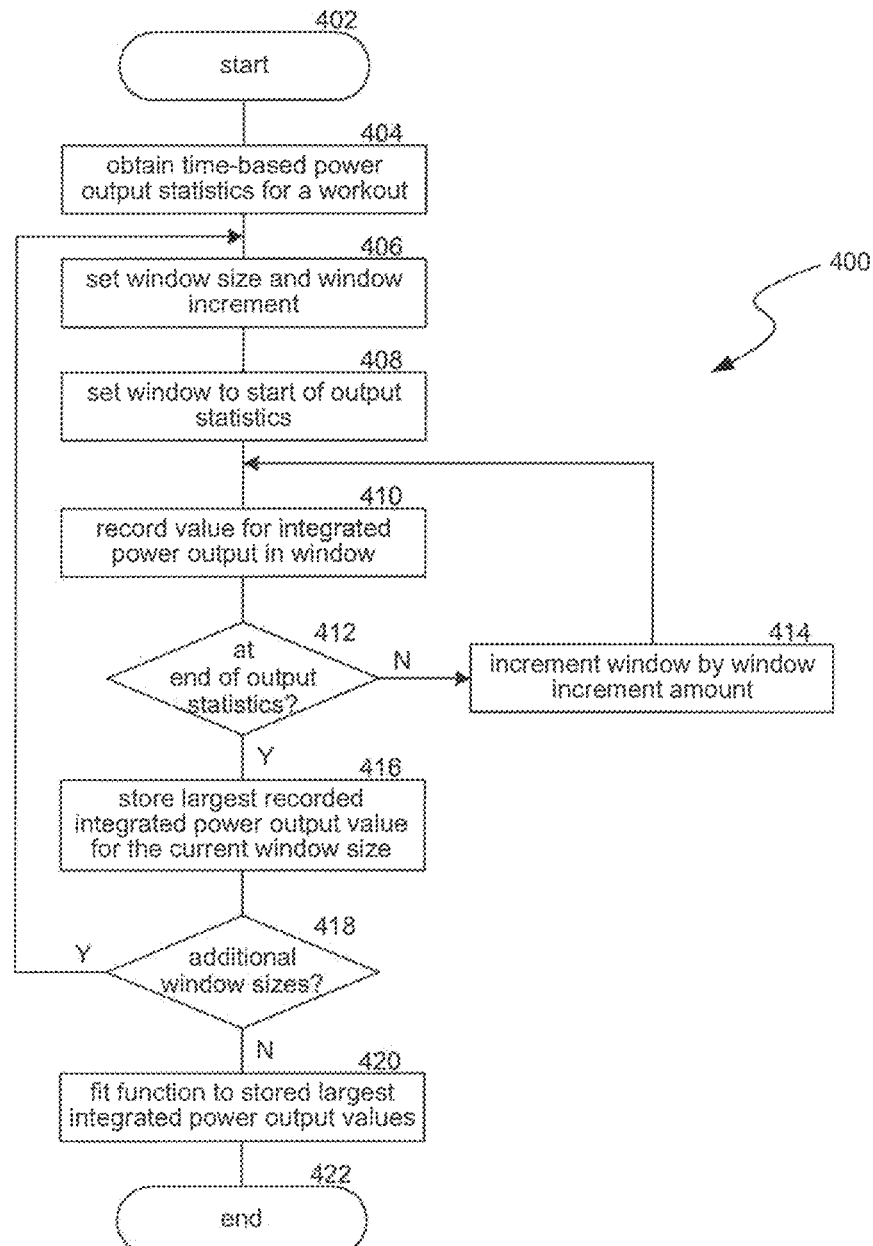
FIG. 4 is a flow diagram illustrating a process used in some implementations for determining a finite work capacity and critical power using time-based power output statistics.

FIG. 4 is a flow diagram illustrating a process 400 used in some implementations for determining an ability function or user's finite work capacity and critical power based on time-based power output statistics. Process 400 begins at block 402 and continues to block 404. In some implementations, process 400 can be performed continuously, e.g. as workout information is fed into an adaptive training system during the workout. In some implementations, process 400 can be performed ahead of time, e.g., based on a received log of the user's workout data.

At block 404, process 400 can obtain time-based power output statistics for a workout or set of workouts. In various implementations, the power output statistics can be automatically gathered from instrumentation on a workout apparatus (e.g. treadmill, elliptical, bike, fitness tracker, etc.), can be entered through a user interface (e.g. entering a run duration and distance), or can be a log of one or more previously recorded workouts. In some implementations, power data can be based on combinations of measures such as speed or distance and time, where a default force for a workout type can be used to estimate work per time, i.e. power. In some implementations, the force can also be, at least in part, measured, e.g. based on a resistance or incline setting. In some implementations, user biographic specifics such as height, weight, gender, and age, are provided in a user profile. These user biographics can be used to more accurately convert workout measurements, such as distance run in an amount of time, into a power measurement. However, process 400 can use some default values to determine power measurements based on a user's workout performance, and thus generate a user's critical power and finite work capacity without the user's biographics. This allows users to use these versions of the system without requiring an extensive profile creation process, and thus users have a low barrier to entry for the system.

In the outer loop between blocks 406-418, process 400 can iteratively divide the power output statistics into segments of the time domain, or "windows," where the window size increases by an incremental amount in each iteration of this outer loop. For all of the windows with a particular size, the window with a largest determined integrated power (work) value in a particular iteration can result in a data point. The work value for a particular window can be computed by taking the area under the power curve defined by the power output statistics in that time window. The largest of these work measures for any window of a particular size is an estimation of the maximum amount of work that user can perform in the amount of time defined by the window size. The resulting set of data points can be used to determine an ability function, which can in turn be used to determine a critical power and finite work capacity for that user.

At block 406, process 400 can set a window size and a window increment. A window size can be an interval of time from which an individual data point can be extracted from the obtained power output statistics. For example, if the obtained power output statistics provide power output values at increments of a 30 minute workout, a window size can be the size of various "windows" of the 30 minute dataset. One window will produce a stored data point from each set of windows that all have the same size. The window increment can be a value by which the start and end of a previous window are incremented to obtain a next window. In some implementations, windows can be overlapping, meaning the window increment is set to a value less that the window size. In some implementations, the windows can be non-overlapping, meaning the window size and window increment are set to the same value. In each iteration of the loop between blocks 406-418, process 400 can generate a single data point corresponding to the window size used in that iteration. In each subsequent iteration, a new window size is selected at block 406. In some implementations, these window sizes can start at a particular size (e.g. 1 second, 5 seconds, etc.) and be increased by a set amount or percentage in each subsequent iteration of the loop. For example, the first window size could be 1 second and window sizes are increased by 10% in each subsequent iteration, so the first five window sizes would be 1 second, 1.1 seconds, 1.21 seconds, 1.33 seconds, and 1.46 seconds. As another example, the first window size could be 5 seconds and window sizes are increased by 1 second in each subsequent iteration, so the first five window sizes would be 5 seconds, 6 seconds, 7 seconds, 8 seconds, and 9 seconds.

At block 408, process 400 can set an initial window for the current window size by starting the window at the start of the obtained time-based power output statistics (e.g. at time_zero) and ending the window at the start of the obtained time-based power output statistics plus the window size (e.g. time_zero+window_size). In the inner loop between blocks 410-414, process 400 can slide the window for the current window size over the time-based power output statistics to determine (at block 416) at which point the area under the curve, defining the power output statistics, within the window size, is largest. While process 400 describes this in terms of incrementing a window's start/end points, other procedures can be used to determine which area under the curve, for the window size interval, is largest. At block 410, process 400 can record an integrated power (work) value from the current window, i.e. the integration or area under the curve for the power/time graph of the obtained power-based statistics. An example of this process is provided below in relation to FIGS. 5A-E. Each recorded value can be a point having window size (e.g. seconds) as the x-axis and work done (e.g. joules) as the y-axis.

At block 412, process 400 can determine if the end of the current window is at least at the end of the obtained time-based power output statistics. If so, each window of the current window size into the time-based power output statistics has been analyzed, the inner loop between blocks 410-414 is complete, and process 400 continues to block 416. If not, at least one window into the time-based power output statistics has not yet been analyzed, the inner loop between blocks 410-414 is not complete, and process 400 continues to block 414. At block 414, process 400 can increment the start and end of the current window by the window increment. This creates a new current window for a value to be recorded from, at block 410.

At block 416, process 400 can review all the values recorded at block 410 for the current window size and store the largest value corresponding to the current window size. This value indicates a measure of the most amount of work the user can perform in a given amount of time. In some implementations, the value stored corresponding to the current window size can be the largest of the recorded values, an average of a top amount (e.g. top 5 or top 10%) of the recorded values, or the top value that is within a certain standard deviations of the median of the recorded values. In some implementations, once a value is stored at block 416, the memory storing the values recorded at block 410 can be freed.

At block 418, process 400 can determine if there are additional window sizes to use in a further iteration of the loop between blocks 406-418. For example, process 400 can use a specified number of window sizes, can increment the window sizes a certain amount until a threshold is reached or until the window size is at least a specified percentage of the total time covered by the time-based power output statistics, or can have a specified set of window sizes to use. If there are additional window sizes to use, process 400 continues back to block 406, where the next window size is set. Otherwise, process 400 continues to block 420.

At block 420, process 400 can fit a function to the values stored at block 416. This function can have the window size (e.g. seconds) on the x-axis and work (e.g. joules) on the y-axis. In various implementations, the function can be of a specified degree, e.g. a first degree function (linear), a second degree function (quadratic), third degree (cubic), etc. In some implementations, in addition to the data points stored at block 416 for the obtained time-based power output statistics, the function can be fit to additional stored data points, e.g. from other workout statistics that were windowed in a process similar to the one described for blocks 404-418. In some implementations, process 400 can fit a function to data points that are not from a windowing process. For example, where power output statistics are not known for multiple points across a workout, work vs. time measures from single workout instances can be used as data points and the function is fit to this set of data points.

In some implementations, various procedures can be applied to adjust for the age of the stored power output values or anomalies among the stored power output values. In some implementations, this adjustment can include smoothing the curve of the function, e.g. applying a Gaussian kernel. In some implementations, this adjustment can include limiting the number of data points that are looked at for a given window size. For example, only data points for a window size that are no more than six weeks old are used or only the most recent six data points are used. In some implementations, the value of each data point can be weighted (decayed) based on its age. Various decay functions can be used to accomplish the weighting, such as exponential decay. For example, the value of each data point can be multiplied by $0.99^{\wedge}(age\_in\_weeks)$. As another example, each data point can be multiplied by $e^{\wedge}(V*age)$, where V can be a value less than 1, such as 0.0004, and the age can be in various increments, such as days since the workout that generated the data point.

In some implementations, where there are multiple data points for a single window size (e.g. from different workouts), the function can be fit to only the largest work data point for each window size (or the largest after any applied weighting). In some implementations, once a function is fit to the stored data points, the memory storing data points that were not used as part of the fit, e.g. because there was a larger data point for the same window size, can be freed.

The function fit to the data points representing a user's maximum power output ability in a timeframe can specify a critical power (CP) for the user. This fitted function can also specify a finite work capacity (W') for the user. The critical power can be the slope of the function or, where the function is non-linear, a slope of the function between two points of the function. Thus, the critical power can represent an amount of additional work the user can perform given any specified amount of additional time. The finite work capacity can be the y-intercept (a work output, e.g. joules, value) of the function. Thus, the finite work capacity represents an amount of initial work the user can perform given no extra time.

In some implementations, the determined critical power and finite work capacity can be used to generate a new ability function that more accurately defines the user's abilities, particularly in early intervals of a workout, such as in the first 60 seconds. For example, a function can be more accurate where it accounts for real-world circumstances such as the fact that given zero time a user's ability to perform work is also zero. In some implementations, this new ability function can be a combined linear and logarithmic function. For example, the ability function can be specified as $W=CP*t+W'*\log(t+1)$, where W is a work ability (dependent variable) and t is a given amount of time (independent variable). Using this new ability function provides more stable and robust fit optimization as it accounts for the time dependent curvature seen in the data.

Process 400 can return these determined critical power or finite work capacity values and end at block 422. In some implementations, instead of determining and returning critical power and finite work capacity values, the function fit to the data points can be returned.

Figure 5A:
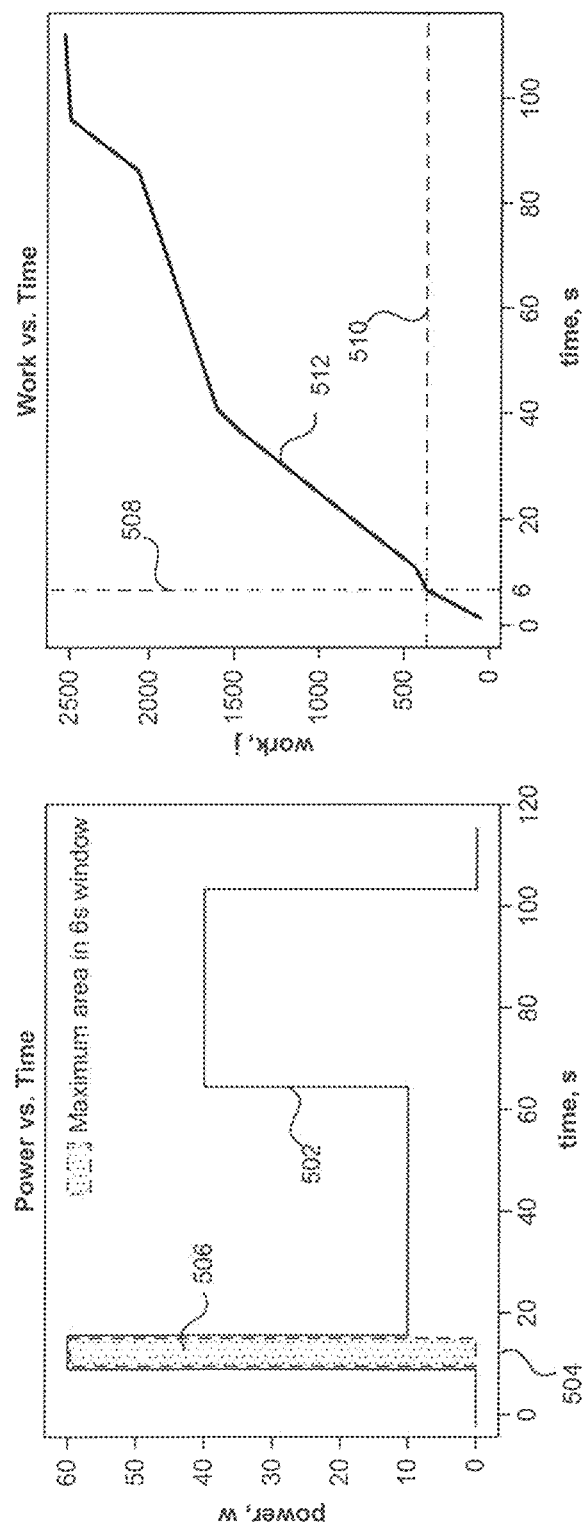
FIGS. 5A-E are conceptual diagrams illustrating an example of windowing power output statistics to determine maximum work data points.

FIGS. 5A-E are conceptual diagrams illustrating an example of windowing power output statistics to determine maximum work data points. These maximum work data points can then be used to compute an ability function. FIGS. 5A-E show an example implementation of the loop between blocks 406-418. FIG. 5A shows step 500 of this example where power output statistics for a workout have been graphed as function 502 and the window size has been set to six seconds. A particular window 504 has been determined to correspond to the largest area 506, under function 502, for a six second window size. A data point corresponding to this largest area 506 is added to the work vs. time graph 512, at the intersection of line 506 (six seconds—the window size) and line 510 (360 joules—area 506).

Figure 5B:
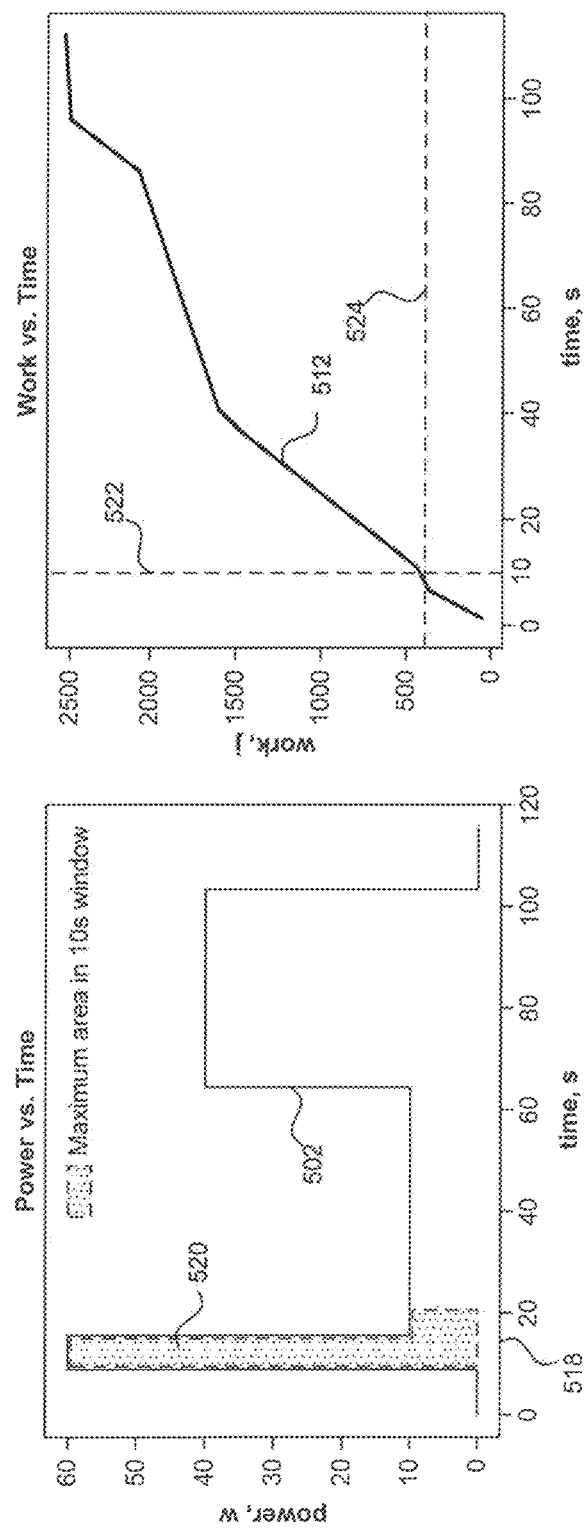

FIG. 5B shows step 515 of this example. A next window 518 has been determined to correspond to the largest area 520, under function 502, for a ten second window size. A data point corresponding to this largest area 520 is added to the work vs. time graph 512, at the intersection of line 522 (ten seconds—the window size) and line 524 (400 joules—area 520).

Figure 5C:
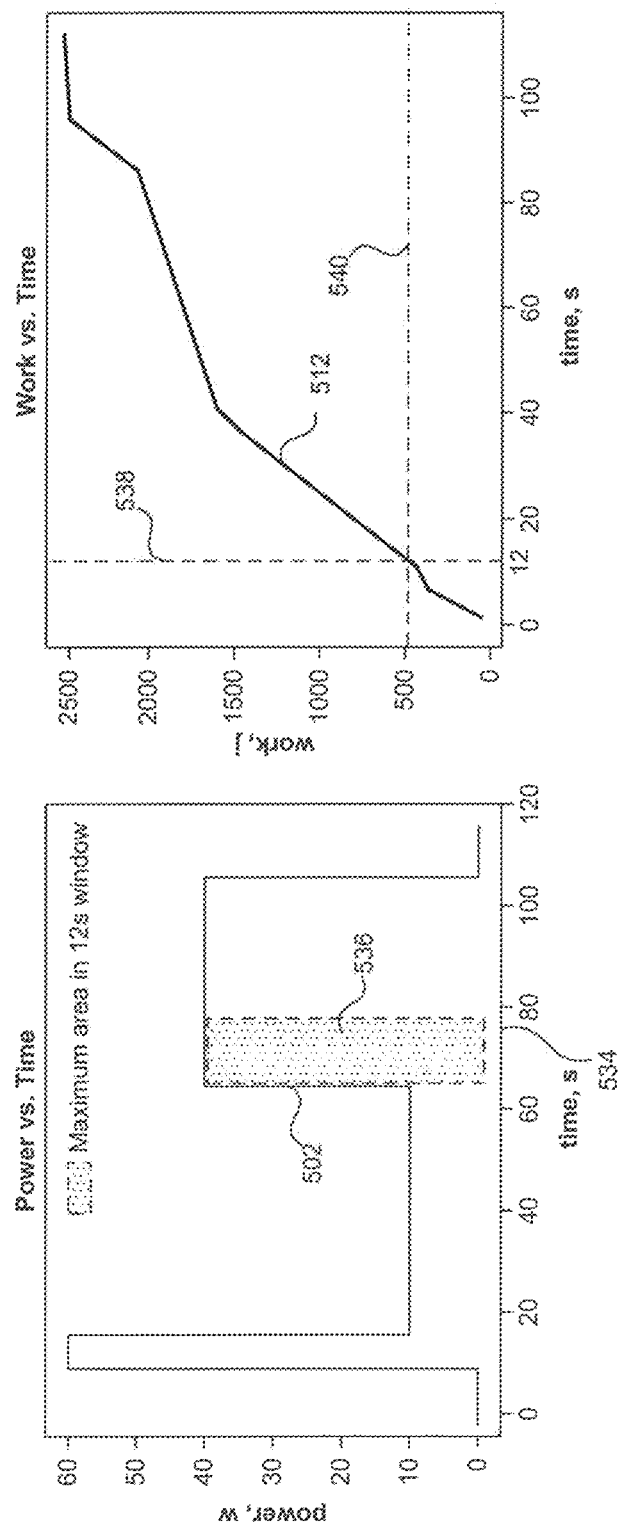

FIG. 5C shows step 530 of this example. A next window 534 has been determined to correspond to the largest area 536, under function 502, for a twelve second window size. A data point corresponding to this largest area 536 is added to the work vs. time graph 512, at the intersection of line 538 (twelve seconds—the window size) and line 540 (500 joules—area 536).

Figure 5D:
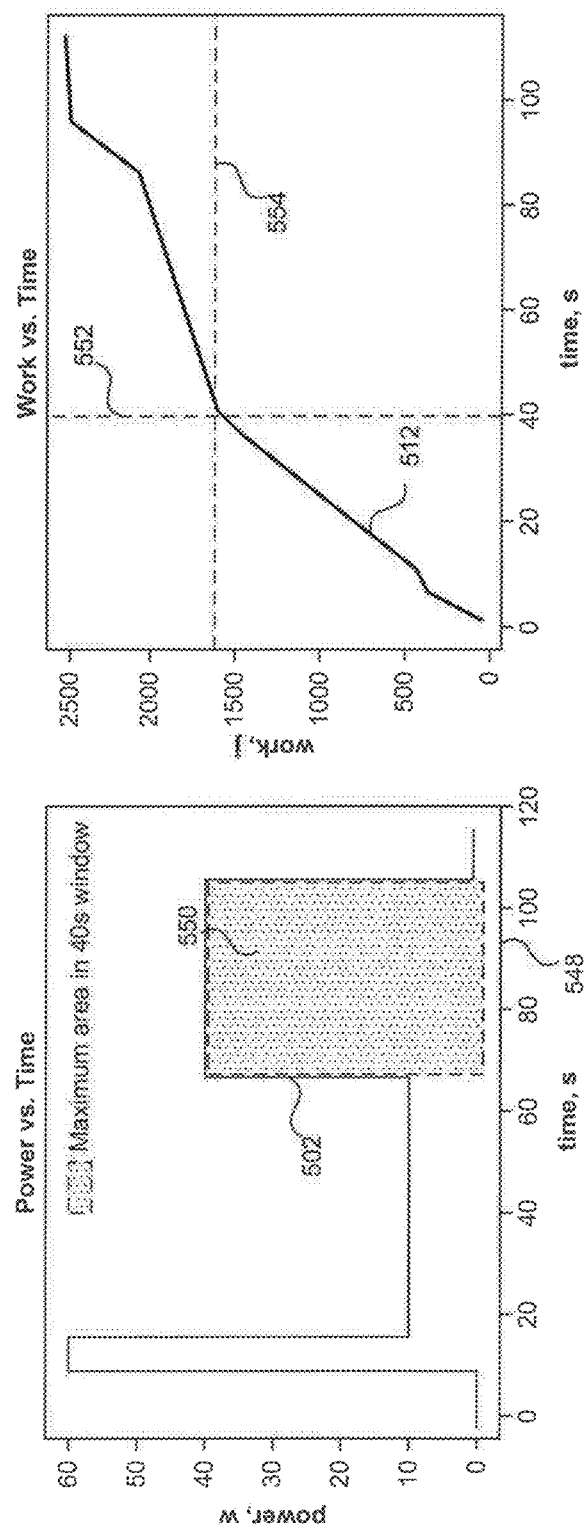

FIG. 5D shows step 545 of this example. A next window 548 has been determined to correspond to the largest area 550, under function 502, for a forty second window size. A data point corresponding to this largest area 550 is added to the work vs. time graph 512, at the intersection of line 552 (forty seconds—the window size) and line 554 (1667 joules—area 550).

Figure 5E:
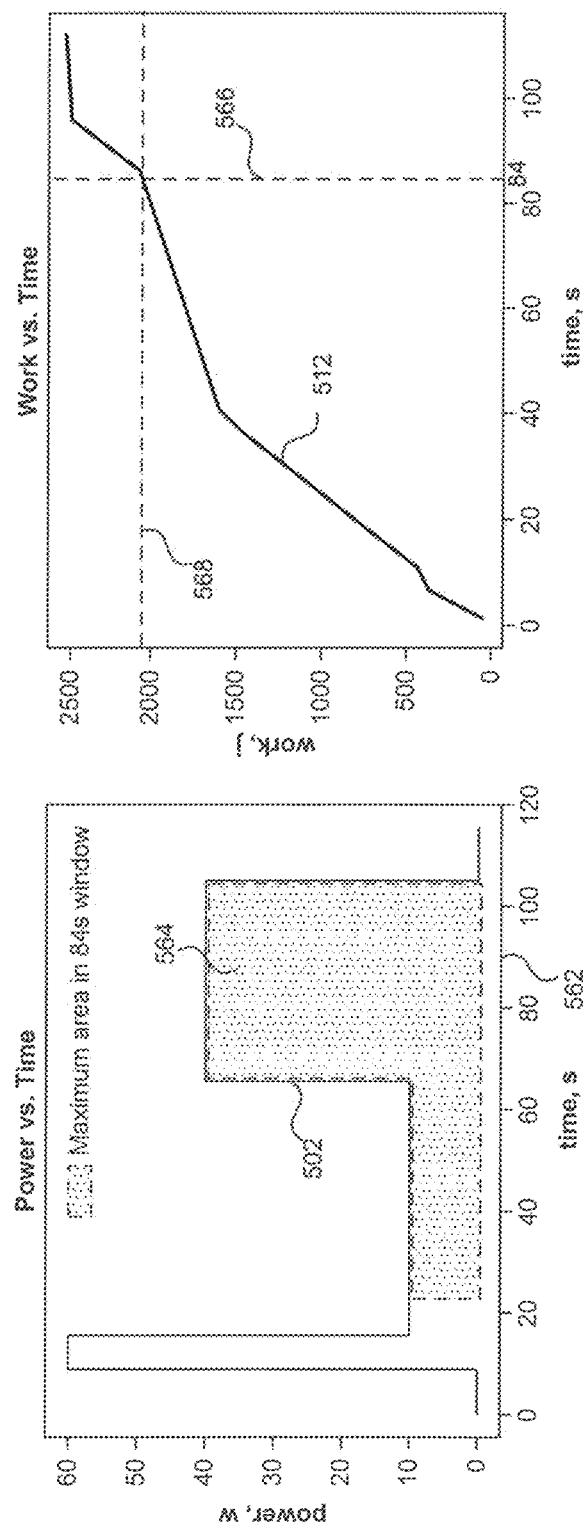

FIG. 5E shows step 560 of this example. A next window 562 has been determined to correspond to the largest area 564, under function 502, for an eighty-four second window size. A data point corresponding to this largest area 564 is added to the work vs. time graph 512, at the intersection of line 566 (eighty-four seconds—the window size) and line 568 (2065 joules—area 564).

Once the data points identified in FIGS. 5A-E are known, they can be used to define an ability function. In some implementations, work vs. time graph 512 can be the user's ability function. In some implementations, the ability function can be a border specified by these data points, where the border can limit maximum workout parameters as described in relation to FIG. 6. In some implementations, another function can be fit to these data points to define the ability function. In some implementations, the fitted function can then be used to determine a critical power and finite work capacity. FIGS. 5A-E provide sample window sizes from a single workout. In other embodiments, window sizes can be larger or smaller or can be more or less numerous. An example is provided next in FIG. 5F that uses other data points from multiple workouts, with more window sizes, to generate an ability function.

Figure 5F:
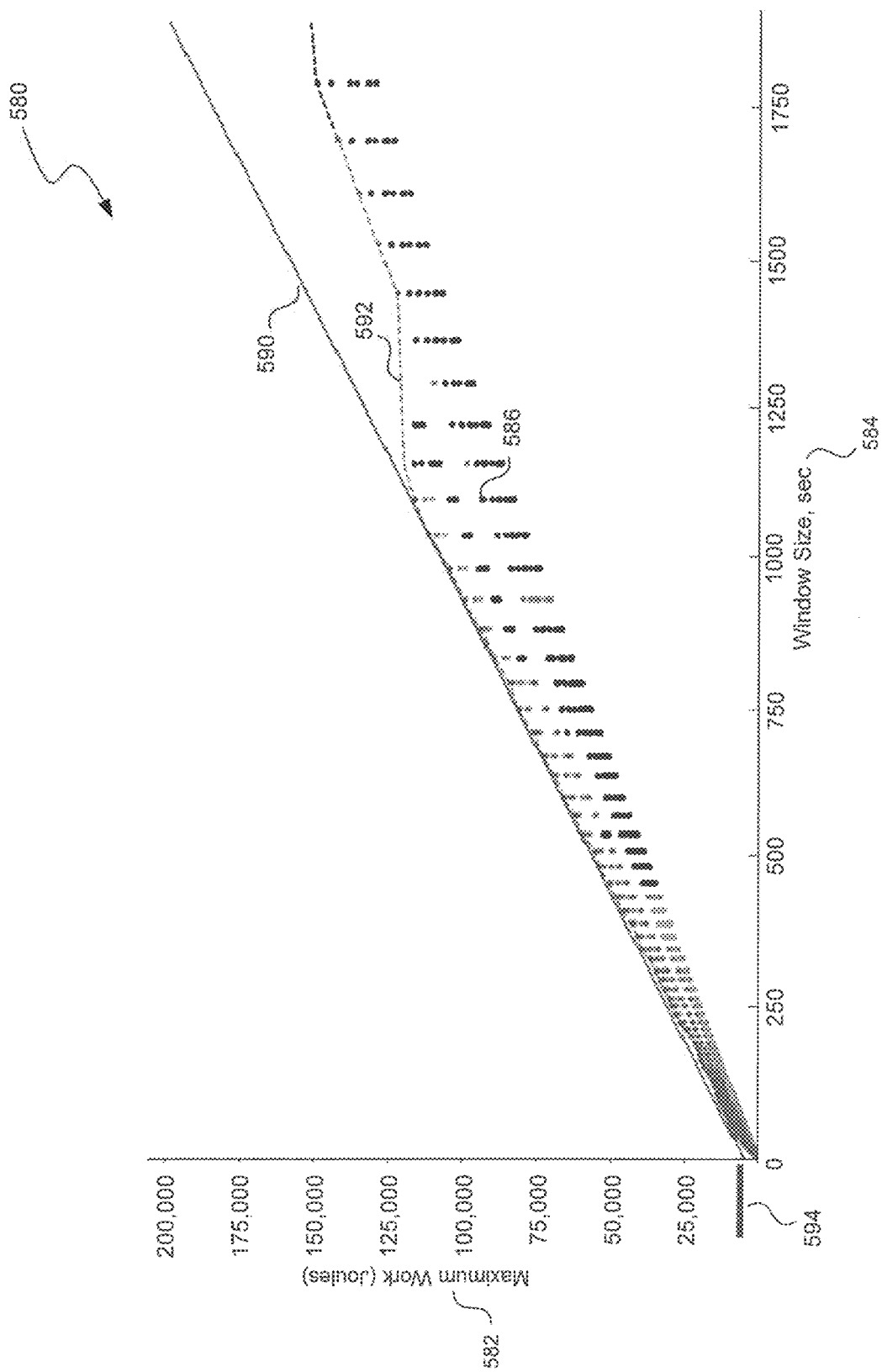
FIG. 5F is a conceptual diagram illustrating an example with a function fit to a series of data points determined through windowing of time-based power output statistics.

FIG. 5F is a conceptual diagram illustrating an example 580 with a function fit to a set of data points for determining a user's critical power and finite work capacity. The function is computed by determining a fit to a series of data points that were obtained through windowing of time-based power output statistics, as shown in FIG. 4. FIG. 5F shows work 582 (y-axis, in joules) vs. time 584 (x-axis; in seconds).

Example 580 includes a set of data points, such as data point 586. Each data point is the largest work value data point, from a set of possible work value data points each corresponding to a particular window size, from a workout. In example 580, a set of possible data points (not shown) were taken at block 410 with a window size of 1150 seconds, and one representing the largest amount of work done (i.e. area under the power output curve) in an 1150 second window of the workout was stored at block 416, as data point 586. An example of this process is provided in FIGS. 5A-E. The additional data points at the 1150 seconds mark above and below data point 586 are from statistics taken from other workouts.

In example 580, line 590 was a best-fit to the largest of the data points for each window size from the various workouts. In some implementations, process 400, at block 420, can determine where a performance boundary is for a user as a location, after an initial threshold, where further data points no longer increase in value with a slope that is relatively consistent. This demonstrated performance boundary is shown in example 580 by dashed line segments 592. The fit of line 590 is fit to the largest of the data points for each window size before the split at the beginning of the performance boundary. The slope of line 590 is used as the critical power. Example 580 also shows where, at 594, line 590 crosses the y-axis 582, which is used as the finite work capacity.

Figure 5G:
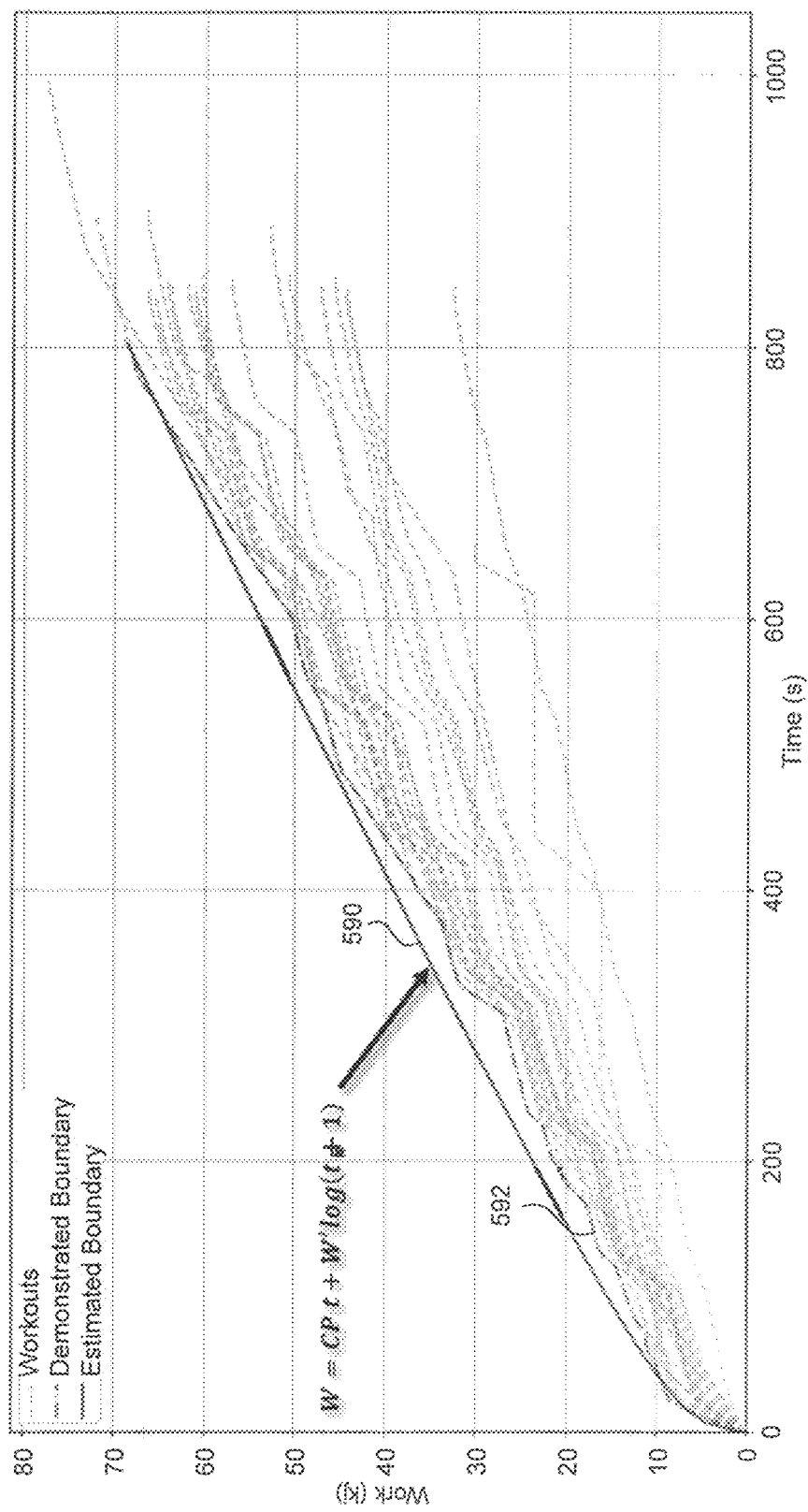
FIG. 5G is a conceptual diagram illustrating an example with a combined linear and logarithmic performance ability function generated based on a determined finite work capacity and critical power.

FIG. 5G is a conceptual diagram illustrating an example with a combined linear and logarithmic performance ability function generated based on a determined finite work capacity and critical power. In this example, a critical power (CP) and finite work capacity (W') have been determined. These values are used to generate a new ability function 590, defined by the formula $W = CP*t \; W'*\log(t+1)$, where W is a work ability (dependent variable) and t is a given amount of time (independent variable). This new ability function 590 is a better fit to the performance boundary 592, particularly in the first 60 seconds of the work data.

Figure 6:
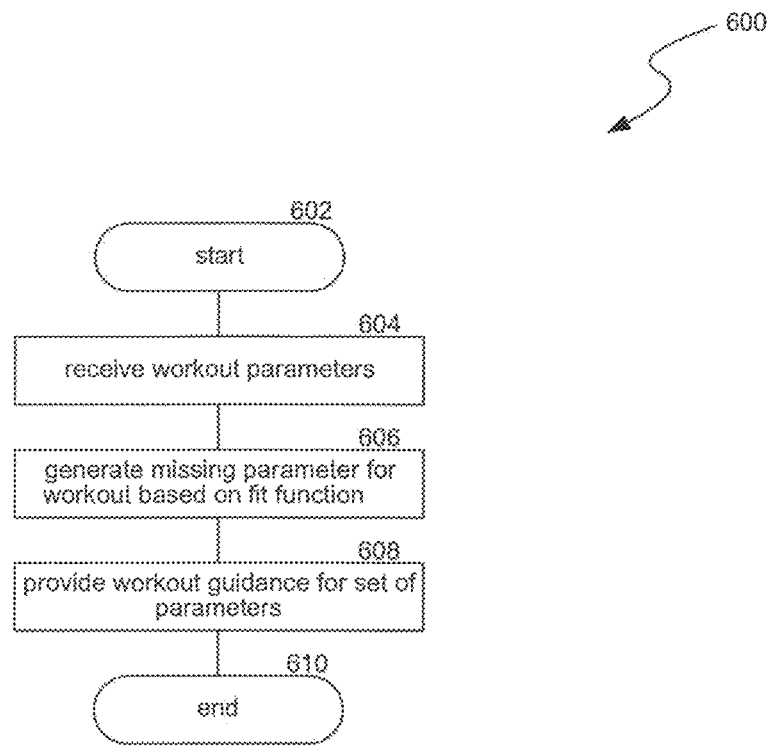
FIG. 6 is a flow diagram illustrating a process used in some implementations for translating a determined fit function into a training program based on workout parameters.

FIG. 6 is a flow diagram illustrating a process 600 used in some implementations for determining a user-specific training program by determining workout parameters based on the user's determined critical power or ability function. In some implementations, process 600 can be performed continuously, e.g. as workout information is fed into an adaptive training system during the workout. In some implementations, process 600 can be performed ahead of time, e.g. to generate a training session for a user prior to the user beginning the workout. Process 600 begins at block 602 and continues to block 604.

An adaptive training program can include one or more workouts and each workout can be defined by a set of parameters mapping the workout into work values given time. For example, when defining a sprint exercise for a user, the parameters can be simply duration and power output during the sprint. As another example, for an interval workout with regular intervals, the parameters can be: number of intervals, interval duration, power output during intervals, rest duration, and power output during rests. As a further example, for an interval workout with "skip intervals," the parameters can be: number of intervals, duration of peak work during interval, duration of short rest time within an interval, power output during interval peak, rest duration between intervals, and power output during rests. In some implementations, workouts can also include a difficulty factor parameter, which specifies how close to the user's maximum work capacity the workout should bring the user.

At block 604, process 600 can receive a partial set of parameters for a workout. In some implementations, the parameters received at block 604 can be all but one of the parameters needed to specify the workout. For example, for the interval workout with regular intervals, all but the parameter defining the number of intervals can be provided. In some implementations, one or more of the workout parameters can be set by various methods, such as by user input, using default values, using values established to further certain goals (e.g. increase critical power ability; increase finite work capacity ability; increase sprint ability by having shorter more intense workouts; or endurance with longer, less intense workouts), etc. In some implementations, the workout parameters can be restricted to certain values, e.g. maximum or minimum time or number or duration of intervals, etc. These restrictions can be in place so that the remaining parameter determined by the system is realistic (Le, it doesn't suggest a workout of two days or of twelve seconds) or so that a workout based on the parameters is easier to follow (e.g. interval length is a round number).

At block 606, process 600 can use the received workout parameters and a user ability indicator comprising one or more of: critical power and finite work capacity values for a user, a "fit function" defined by a function fit to a set of workout statistics in work vs. time, or the set of workout statistics in work vs. time as a defined border. In some implementations, the user's user ability indicators can be computed each time they are needed, e.g. by executing process 400. In some implementations, instead of recomputing the user's ability indicators from all available workout data, stored previous versions of the user's ability indicators can be updated to account for new workout data that has been obtained since that stored ability indicators were generated. For example, the stored user's ability indicators can be weighted based on the age of the underlying data and can be updated with each workout set. In various implementations, this updating can be performed to generate new user ability indicators when new workout data is received, when a determination of a user's ability indicators are needed, at a given interval (e.g., daily, weekly, etc.), or based on available resources (e.g., at night when server availably is typically high, according to a current measure of server resource availably, etc.).

Process 600 can then use the workout parameters and user ability indictor to compute the missing parameter defining the workout to be specific for the user. For each type of workout, a transform can be determined to map a function defining the workout (based on the workout parameters) in terms of work vs. time. The function defining the workout can be specified such that it does not exceed an "ability line" for the user, defined by the received user ability indicator. In various implementations, the ability line can be the ability function, the defined border, or a line determined by setting the user's critical power as the slope and the user's finite work capacity as the y-intercept. The point where the workout function intercepts the ability line is the exhaustion point, i.e. the point where the user is expected to no longer be able to perform any work at the same intensity level. Examples of such parameterization and comparison are provided below in relation to FIG. 7 and the Appendix. In some implementations, the ability line can be decreased (the y-intercept can be decreased with the same slope) so that the user is only expected to come within a threshold amount of a total exhaustion point. In some implementations, a default y-intercept can be set, (e.g. 0). For example, this can be done when only the critical power of a user is available or where it will be a particularly lengthy workout.

At block 608, process 600 can provide a user specific training program based on the now complete set of workout parameters. For example, process can indicate a workout duration, can cause a setting to be established on a workout machine, can integrate the workout into a set of multiple workouts, etc. In some implementations, process 600 can continually monitor power output during the user's workout, update the user's ability function for the observed power output, and update the workout parameters accordingly. Process 600 can then provide further updates to the user, such as suggesting they slow down if they are expected to hit their exhaustion point before the workout is scheduled to end or that they should speed up if they are not expected to reach a goal.

Figure 7:
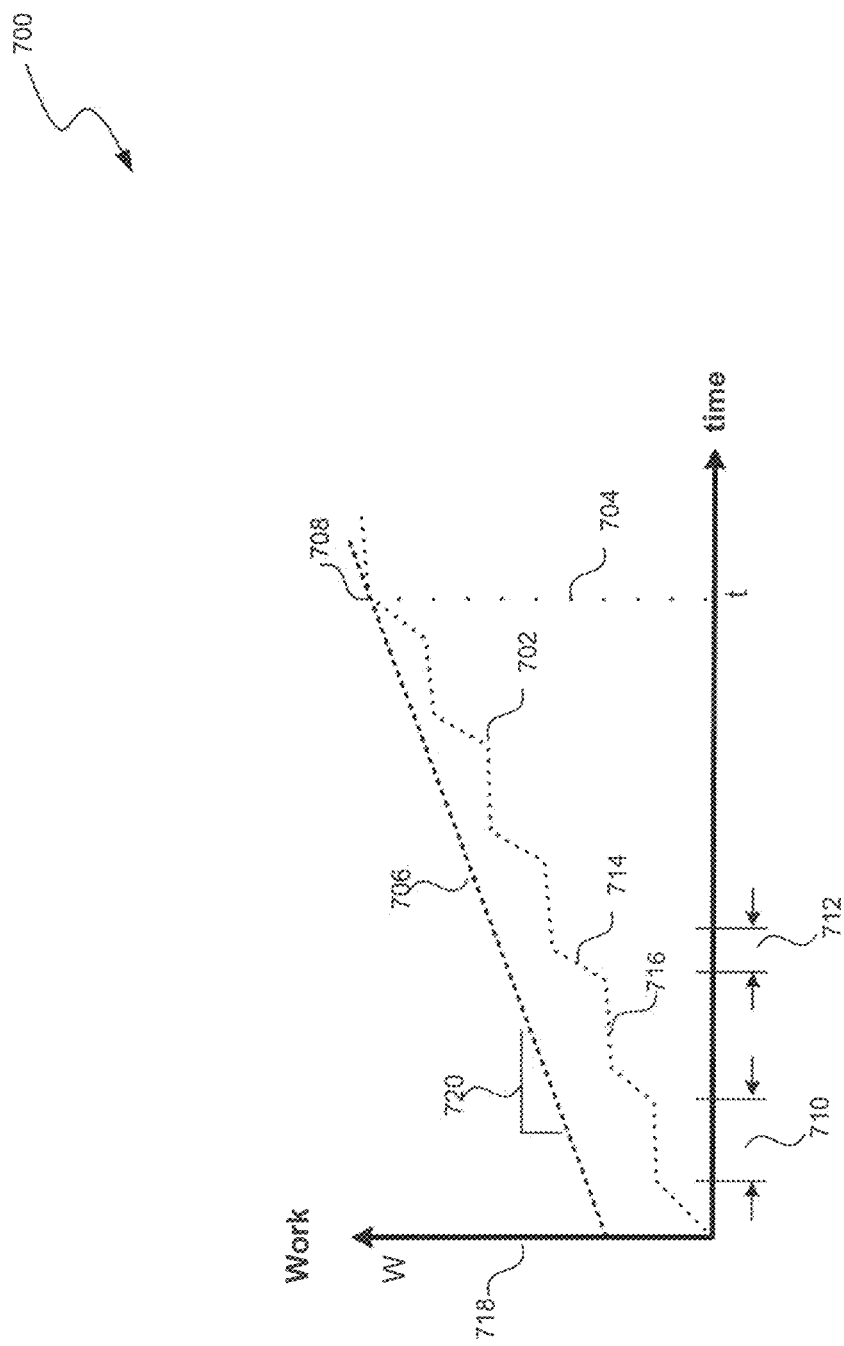
FIG. 7 is a conceptual diagram illustrating an example representation of a workout function computed by determining a parameter to keep the workout function below an exhaustion point, based on fit function parameters.

FIG. 7 is a conceptual diagram illustrating an example 700 representation of a workout function 702 for a user specific workout. The user specific workout is computed by determining a time parameter 704 which keeps all values of the workout function 702, during the workout, below the user's ability line 706.

In example 700, a user's critical power and finite work capacity are known, e.g. through an execution of process 400. The user's ability line 706 is generated by setting the critical power as the slope 720 and the finite work capacity as the y-intercept 718.

In example 700, the workout is an interval workout with regular intervals. The duration of the rest period 710 and high intensity period 712 are set by a user through a user interface and the slope of the line segments 714 during the high intensity segments are set to a first default value based on an expect running rate during these high intensity portions the slope of the line segments 716 during the rest segments are set to a second default value based on another expect running rate during the rest portions.

The adaptive training system determines the intersection between the user's ability line and the function representing the workout, i.e. exhaustion point 708. The time value 704 for the exhaustion point is the time determined for this workout such that the user reaches her exhaustion point. Additional details on how the adaptive training system can perform these operations are provided in the appendix.

Figure 8A:
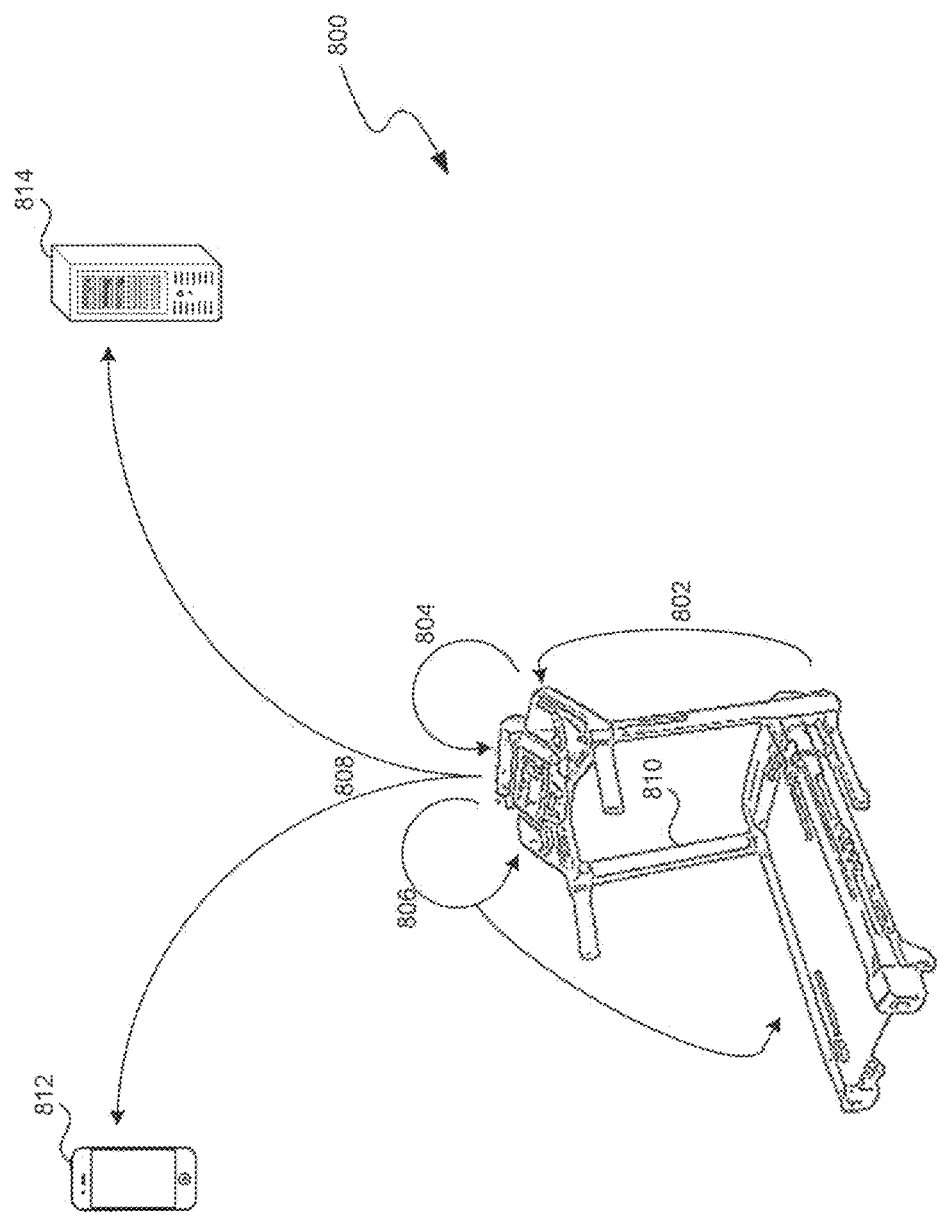
FIGS. 8A-C illustrate example system configurations that implement versions of an adaptive training system.
Figure 8B:
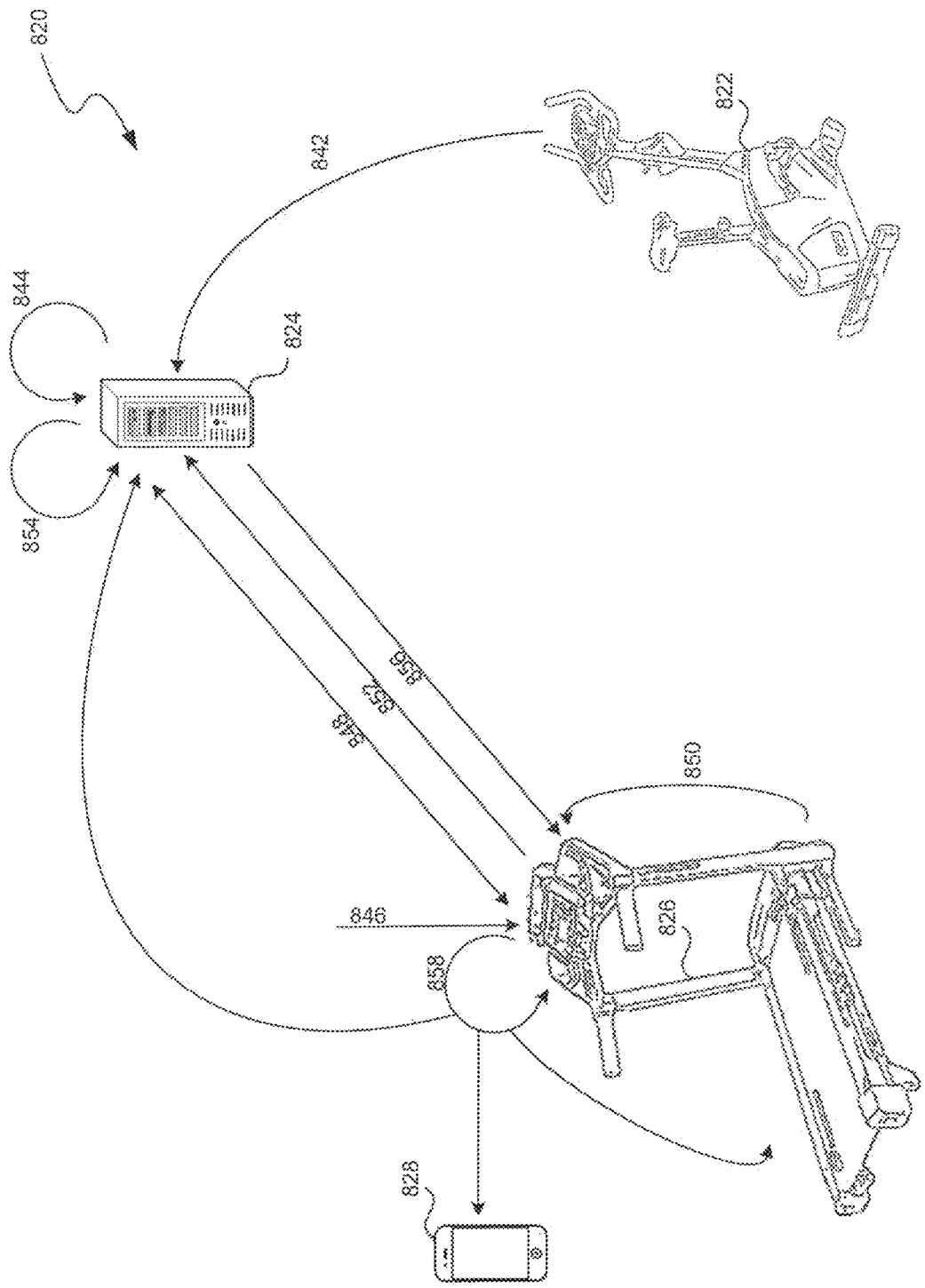
Figure 8C:
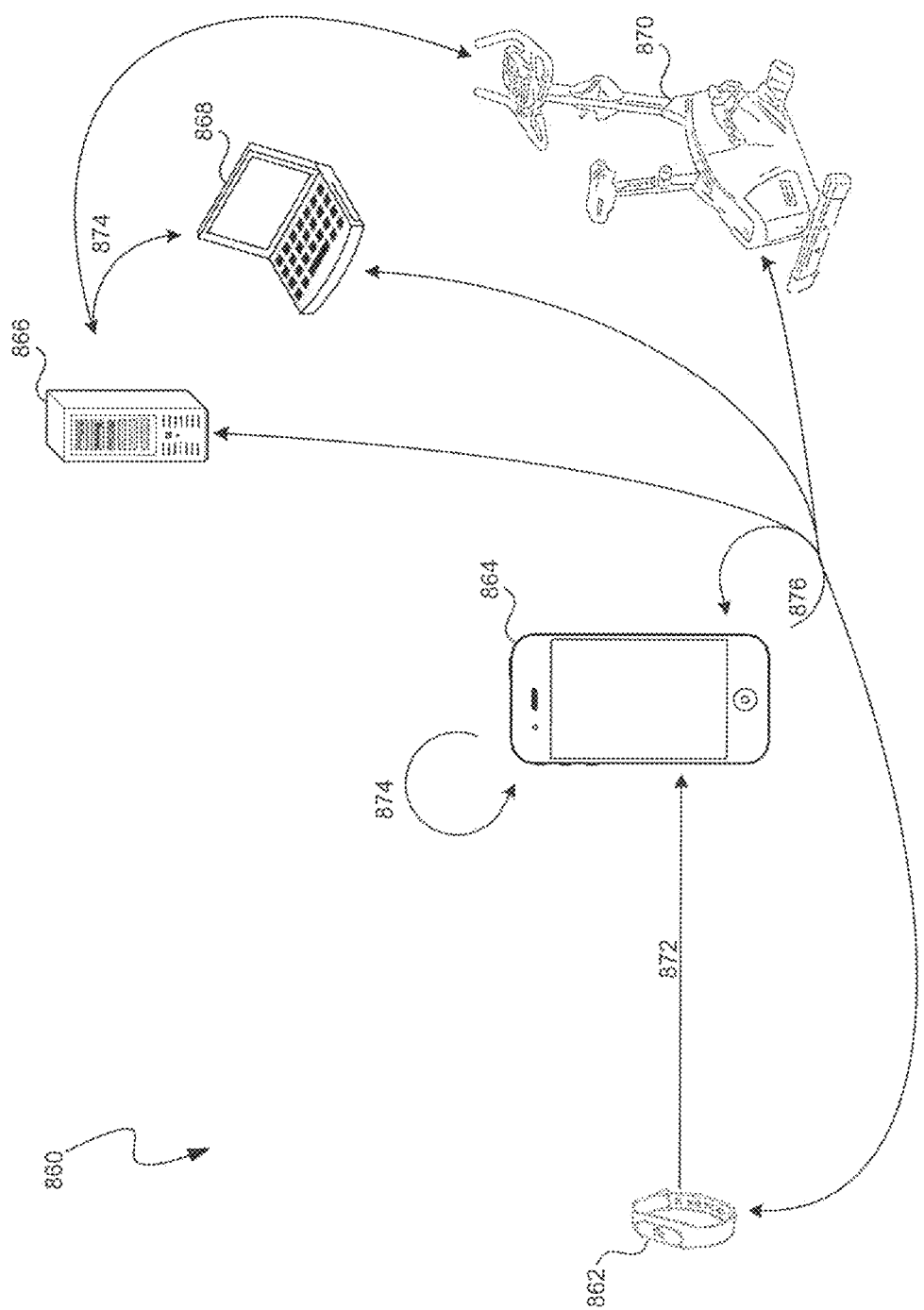

FIGS. 8A-C illustrate examples 800, 820, and 860, showing system configurations that implement versions of an adaptive training system. In FIG. 8A, example 800 shows a configuration where the adaptive training system is integrated into workout machine 810. Example 800 begins with measurements indicative of a user's power output, such as speed and incline, being recorded during a workout session. At 804, circuitry in the workout machine transforms the power measurements into values of work. The circuitry then uses these values of work to determine a user's ability function and uses the ability function to generate a training program. In some implementations, step 804 can be accomplished using processes 400 and 600. For example, workout machine 810 can use the power measurements to determine work points and then fit the work points to an ability line. The workout machine can use the ability line and parameters that the user has specified for the workout to generate a training program specifying other, previously unknown workout parameters that keeps the user below his or her expected exhaustion point. For example, the user can specify parameters such as duration and interval length and the workout machine can generate a training program specifying an incline for each interval that keeps the user below his or her expected exhaustion point.

The training program can be used, at 806, to automatically control functionality of the workout machine, such as by setting speed, duration, or incline settings. In addition or alternatively, the resulting training program can be used, at 806, to provide an output on a display of the workout machine or associated device (e.g. a user's paired mobile device). The output can display statistics about the workout, instructions for performing the training program, etc. While example 800 can end when the workout session ends, in some implementations, data from the workout session can be stored at 808. For example, this data can include determined maximum work points, an ability function, workout duration, speed, calories burned, etc. This data can be sent to the user's mobile device or to a server. The system can store this output in association with a user profile.

In FIG. 8B, example 820 shows a configuration where the adaptive training system is implemented in a network of workout machines, such as workout machines 822 and 826. In example 820, the workout machines are connected via server system 824. In example 820, a user previously used workout machine 822. Workout machine 822 can send, at 842, an identification of the user and data from that workout to server system 824. For example, this data can include determined maximum work points, an ability function, workout duration, speed, calories burned, etc. At 844, server system can use the received workout data to determine a user ability function. In some implementations, step 844 can also include determining a training program for the user.

At step 846, the same user authenticates himself or herself with another workout machine 826. For example, the user can enter a code, scan a barcode on the workout machine using her mobile device (e.g. mobile device 828), or the workout machine can take a reading, such as scanning a code presented by the user, recognizing the presence of the user's mobile device or a FOB, etc. At 848, workout machine 826 and server system 824 can communicate to determine a training program for the authenticated user. In some implementations, the training program can be the one determined at 844, which can be further based on user profile information, such as preferred workout parameters that may include duration, number of intervals, etc. In some implementations, the communication at 848 can include some parameters for the user's next workout, which the server system 824 can use to generate the training program such that the user approaches, but does not surpass, an exhaustion point.

As the user performs the training program, which can be implemented automatically by the workout machine 826 or can be accomplished through instructions provided to the user on how to interact with the workout machine, (not shown), additional measurements indicative of power output can be taken at step 850. In some implementations, the workout machine 826 can autonomously update the training program or workout parameters based on the power measurements, similar to the functions performed by workout machine 810 in example 800. In some implementations, the power measurements can be provided, at 852, to server system 824. The server system, at 854, can update the user's determined ability function. Also at 854, the server system can adjust the training program based on the updated user's ability function. The server system, at 856, can provide the updated training program or workout parameters to the workout machine 826. At 858, workout machine 826 can implement the updated workout parameters, e.g. by providing an updated display on workout machine 826 or on the user's mobile device 828, or by automatically implementing settings on workout machine 828. Also at 858, either as the workout progresses or when the workout ends, workout machine 826 can provide workout data, similarly to step 808 of example 800.

In FIG. 8C, example 860 shows a configuration where the adaptive training system is implemented on mobile device 864. Example 860 begins when mobile device 864 receives workout statistics. In example 860, the workout statistics are obtained from communications with a fitness tracker, however the workout statistics can be obtained from other sources, such as from communication with another type of workout machine, manual user input, logs stored on a server system, etc. At 872, mobile device 864 transforms the workout statistics (e.g. power measurements) into terms of work, uses these to determine a user's ability function, and uses the ability function to generate a training program for the user. In some implementations, step 874 can be accomplished using processes 400 and 600. For example, mobile device 864 can use the power measurements to determine work points and then fit the work points to an ability function. Using the ability function, mobile device can generate a training program, e.g. to determine a run duration or suggested speed, interval lengths, etc. In some implementations, step 874 can be accomplished using processing from a server system, such as server system 866.

The received workout statistics, transformations of these statistics, or resulting training programs can be stored by mobile device 864. While example 860 can end here, e.g. where user data is all stored at the mobile device and training program suggestions are provide through the mobile device, in some implementations, this data can be sent, at 876, to other devices 866-870, e.g. for further analysis (e.g. at server system 866), for automatic control of workout equipment 870, or to be viewed by the user, e.g. through a web interface at a computing device 868. In various implementations, these interactions can be interrelated or facilitated through communications with other devices, e.g. through communications 874.

In various implementations, aspects of the configurations from any of examples 800, 820, and 860 can be combined. For example, input 872 in example 860 can be based on outputs 808 or 858 from examples 800 and 820; server 824 in example 820 in example 820 could be replaced with mobile device 864 from example 860; output 842 in example 820 can be based on output 808 in example 800 or can be output 876 from example 860. Additional configurations, combinations, substitutions and additions are also contemplated. While examples 800, 820, and 860 illustrate several types of devices, in some implementations, the function performed by any one of these devices can be accomplished by the others or by devices not explicitly recited.

The following is a non-exhaustive list of additional examples of the disclosed technology.

1. A workout machine system for automatically providing an adaptive training program, the system comprising:
   a workout apparatus that implements a training session of a particular type, with given parameters;
   an instrument system, integrated with the workout apparatus, that obtains measurements indicative of power output; and
   a processing component configured to generate the adaptive training program by:
      identifying a work value for each particular window size, of multiple window size durations, within the measurements indicative of power output, by:
         identifying a largest integration, of a function specified by the measurements indicative of power output, for an interval matching the particular window size;
      fitting, as an ability function, a function to the identified work values;
      applying, to a workout function defined for the particular type of the training session, the given parameters and at least one additional parameter, such that the value of the workout function does not exceed the value of the ability function for any time during a duration for the training session; and
      using the given parameters and at least one additional parameter to generate the adaptive training program;
   wherein output or settings of the workout apparatus are automatically provided based on the adaptive training program.

2. The workout machine system of example 1,
   wherein the workout machine system further comprises multiple workout machines connected via a network; and
   wherein the fitting the function to the work values identified for the multiple window size durations further comprises also fitting the function to additional work values identified for the multiple window size durations based on measurements indicative of power output taken on one of the networked workout machines other than the workout apparatus.

3. The workout machine system of example 2, wherein the fitting the function to the work values and to the additional work values comprises:

selecting, for each particular window size, the largest value, of the work values and to the additional work values, corresponding to that particular window size; and fitting the function to the selected largest values for the window sizes.

4. The workout machine system of any one of examples 1-3, wherein the processing component is a server system connected to the network.

5. The workout machine system of any one of examples 1-4, wherein the processing component generates the adaptive training program in response to an identification comprising:
   a code indicative of a user, supplied by the user or by a mobile device associated with the user, to the workout apparatus or to the processing component; or
   a code indicative of the workout apparatus, supplied by the user or by the mobile device associated with the user, to the processing component.

6. The workout machine system of example 5,
   wherein the processing component generates the adaptive training program in response to the identification comprising the code indicative of the workout apparatus; and
   wherein the code indicative of the workout apparatus is supplied to the mobile device through an image capture system on the mobile device capturing an alphanumeric code, bar code, or QR code displayed in conjunction with the workout apparatus.

7. The workout machine system of example 5,
   wherein the processing component generates the adaptive training program in response to the identification comprising the code indicative of the user; and
   wherein the code indicative of the user is supplied by the mobile device, through a wireless communication, to the workout apparatus.

8. The workout machine system of any one of examples 1-3 or 7, wherein the processing component is incorporated in the workout apparatus.

9. The workout machine system of any one of examples 1-3 or 7, wherein the processing component is incorporated in a mobile device associated with a user of the workout apparatus.

10. The workout machine system of any one of examples 1-9, wherein the automatically providing the output or settings of the workout apparatus comprises providing the output to a server system, the output comprising at least an indication of the at least one additional parameter.

11. The workout machine system of any one of examples 1-10, wherein the automatically providing the output or settings of the workout apparatus comprises providing output to a mobile device, the output comprising at least an indication of the at least one additional parameter.

12. The workout machine system of any one of examples 1-11, wherein the automatically providing the output or settings of the workout apparatus comprises providing the output to a mobile device, the output comprising data to be operated on by execution of instructions on the mobile device, configured to provide a display for a user to implement the adaptive training program.

13. The workout machine system of any one of examples 1-12, wherein the automatically providing the output or settings of the workout apparatus comprises providing the output to the workout apparatus, the output configured to cause a display of the workout apparatus to provide instructions for the adaptive training program.

14. The workout machine system of any one of examples 1-13, wherein the automatically providing the output or settings of the workout apparatus comprises providing the settings to the workout apparatus, wherein the workout apparatus automatically implements the adaptive training program based on the settings such that the workout apparatus implements the given parameters and the at least one additional parameter.

15. The workout machine system of any one of examples 1-14, wherein the automatically providing the output or settings of the workout apparatus comprises providing the output to a server system or a mobile device, wherein the output is stored in association with a user profile comprising one or more of:
   at least some of the identified work values;
   the ability function;
   statistics of the adaptive training program;
   measures of actual performance during the training session;
   biographic specifics; or
   any combination thereof.

16. The workout machine system of any one of examples 1-15, further comprising an internet-based interface, accessible through a web browser or mobile device application, wherein the internet-based interface provides access to a user profile associated with multiple workouts performed by a user.

17. The workout machine system of any of any one of examples 1-16, wherein the measurements indicative of power output comprise one or more of:
   speed;
   revolutions-per-minute;
   resistance;
   incline;
   distance;
   duration; or
   any combination thereof.

18. The workout machine system of any one of examples 1-17 wherein the ability function is a linear function.

19. The workout machine system of any one of examples 2 or 3,
   wherein the processing component is a server system connected to the network; and
   wherein the server system obtains the additional work values stored in association with a user profile for the user and generates the adaptive training program, both in response to an authentication of the user.

20. The workout machine system of any one of examples 1-19, wherein the particular type is an interval type workout.

21. The workout machine system of example 20, wherein the given parameters for the interval type workout include one or more of: number of intervals, interval duration, power output during intervals, rest duration, power output during rests, or any combination thereof.

22. The workout machine system of any one of examples 1-19, wherein the particular type is a skip interval type workout.

23. The workout machine system of example 22, wherein the given parameters for the skip interval type workout include one or more of: number of intervals, duration of peak work during interval, duration of short rest time within an interval, power output during interval peak, rest duration between intervals, power output during rests, or any combination thereof.

24. The workout machine system of any one of examples 1-23, wherein applying, to the workout function defined for the particular type of the training session, the given parameters and at least one additional parameter comprises:
obtaining a pre-defined function for the particular type of the training session; filling in the given parameters in the pre-defined function; and
solving for the at least one additional parameter, wherein the at least one additional parameter includes exactly one additional parameter; and
wherein using the given parameters and at least one additional parameter to generate the adaptive training program comprises:
selecting data to display instructing a user to perform a workout based on at least the given parameters and the solved at least one additional parameter; or
specifying the settings of the workout apparatus based on at least the given parameters and the solved at least one additional parameter.

25. The workout machine system of example 24, wherein filling in the given parameters in the pre-defined function comprises using one or more default values for one or more of the function parameters that are not included in the given parameters and are not included in the at least one additional parameter.

26. The workout machine system of any one of examples 1-25 wherein the processing component is further configured to:
receive further measurements indicative of power output as the adaptive training program is performed;
identify further work values based on the further measurements indicative of power output;
update the ability function to further fit the further work values;
update one or more of the given parameters or one or more of the at least one additional parameter based on the updated ability function;
generate an updated adaptive training program based on the updated parameters; and
update the output or settings of the workout apparatus based on the updated adaptive training program.

27. A method for providing an adaptive training program, the method comprising: obtaining measurements indicative of power output;
identifying a work value for each particular window size, of multiple window size durations of the measurements indicative of power output, by:
identifying a largest integration, of a function specified by the measurements indicative of power output, for an interval matching the particular window size;
fitting, as an ability function, a function to the work values identified for the multiple window size durations;
computing a value for at least one previously unspecified parameter for a training session, such that values of a workout function, that uses the previously unspecified parameter, do not exceed corresponding values of the ability function for any time during a duration for the training session;
using the at least one previously unspecified parameter to generate the adaptive training program; and
providing output or automatic workout settings based on the adaptive training program.

28. The method of example 27, wherein the measurements indicative of power output are obtained through manual entry by a user.

29. The method of example 27, wherein the measurements indicative of power output are obtained through recorded workout statistics taken by a wearable fitness tracker.

30. The method of example 27, wherein the measurements indicative of power output are obtained through an instrument system integrated into a workout apparatus.

31. The method of any one of examples 27-30,
wherein the method is implemented in relation to multiple workout machines connected via a network;
wherein the measurements indicative of power output are taken from a first of the networked workout machines;
wherein a second set of measurements indicative of power output are taken, from a second of the networked workout machines, which are transformed into additional work values for corresponding window sizes and are weighted based on an age of the second set of measurements; and
wherein the fitting the function to the work values identified for the multiple window size durations further also comprises fitting the function to the additional work values.

32. The method of example 31, wherein the fitting the function to the work values and to the additional work values comprises:
selecting, for each particular window size, the largest value, of the work values and to the additional work values, corresponding to that particular window size; and
fitting the function to the selected largest values for the window sizes.

33. The method of any one of examples 27-32, wherein the method is performed by a server system connected to multiple workout machines.

34. The method of any one of examples 27-33, wherein generating the adaptive training program is in response to an identification comprising:
a code indicative of a user or of a workout apparatus, supplied by the user, by a mobile device associated with the user, or by the workout apparatus.

35. The method of example 34,
wherein the generation of the adaptive training program is in response to the identification comprising the code indicative of the workout apparatus; and
wherein the code indicative of the workout apparatus is supplied to the mobile device through an image capture system on the mobile device capturing an alphanumeric code, bar code, or QR code displayed in conjunction with the workout apparatus.

36. The method of example 34,
wherein the generation of the adaptive training program is in response to the identification comprising the code indicative of the user; and
wherein the code indicative of the user is supplied by the mobile device.

37. The method of any one of examples 27-30 or 36, wherein the method is performed by a workout machine.

38. The method of any one of examples 27-30 or 36, wherein the method is performed by a mobile device associated with a user of a workout apparatus.

39. The method of any one of examples 27-38, wherein providing the output or automatic workout settings comprises providing the output to a server system, the output comprising at least an indication of the at least one additional parameter.

40. The method of any one of examples 27-39, wherein providing the output or automatic workout settings comprises providing output to a mobile device, the output comprising at least an indication of the at least one previously unspecified parameter.

41. The method of any one of examples 27-40, wherein providing the output or automatic workout settings comprises providing the output to a mobile device, the output comprising data to be operated on by execution of instructions on the mobile device, configured to provide a display for a user to implement the adaptive training program.

42. The method of any one of examples 27-41, wherein providing the output or automatic workout settings comprises providing the output to a workout apparatus, the output configured to cause a display of the workout apparatus to provide instructions for the adaptive training program.

43. The method of any one of examples 27-42, wherein providing the output or automatic workout settings comprises providing the automatic workout settings to a workout apparatus, wherein the workout apparatus automatically implements the adaptive training program based on the automatic workout settings such that the workout apparatus implements the given parameters and the at least one previously unspecified parameter.

44. The method of any one of examples 27-43, wherein providing the output or automatic workout settings comprises providing the output to a server system or a mobile device, wherein the output is stored in association with a user profile comprising one or more of:
at least some of the identified work values;
the ability function;
statistics of the adaptive training program;
measures of actual performance during the training session;
biographic specifics; or
any combination thereof.

45. The method of any one of examples 27-44, further comprising providing an internet-based interface, accessible through a web browser or mobile device application, wherein the internet-based interface provides access to a user profile associated with multiple workouts performed by a user.

46. The method of any of any one of examples 27-45, wherein the measurements indicative of power output comprise one or more of:
speed;
revolutions-per-minute;
resistance;
incline;
distance,
duration;
weight,
repetitions; or
any combination thereof.

47. The method of any one of examples 27-46 further comprising:
based on the ability function, determining a critical power and finite work capacity for a user associated with the measurements; and
modifying the ability function into a combined linear and logarithmic function that uses the critical power and finite work capacity.

48. The method of any one of examples 31 or 32,
wherein the method is performed by a server system connected to the network; and
wherein the server system obtains the additional work values stored in association with a user profile for the user and generates the adaptive training program, both in response to an authentication of the user.

49. The method of any one of examples 27-48, wherein the workout function is defined for an interval type workout.

50. The method of example 49, wherein the given parameters for the interval type workout function includes at least three of: number of intervals, interval duration, power output during intervals, rest duration, power output during rests, or any combination thereof.

51. The method of any one of examples 27-48, wherein the workout function is defined for a skip interval type workout.

52. The method of example 51, wherein the given parameters for the skip interval type workout function includes at least three of: number of intervals, duration of peak work during interval, duration of short rest time within an interval, power output during interval peak, rest duration between intervals, power output during rests, or any combination thereof.

53. The method of any one of examples 27-52,
wherein computing the value for the at least one previously unspecified parameter comprises:
obtaining the workout function, from a set of pre-defined functions, based on an indicated workout type for the adaptive training program;
filling in one or more given parameters in the pre-defined workout function; and
solving for the at least one previously unspecified parameter, wherein the at least one previously unspecified parameter includes exactly one parameter; and
wherein using the at least one previously unspecified parameter to generate the adaptive training program comprises:
selecting data to display instructing a user to perform a workout based on at least the at least one previously unspecified parameter; or
specifying the output or automatic workout settings based on the at least one previously unspecified parameter.

54. The method of example 53, wherein filling in the one or more given parameters in the pre-defined function comprises using one or more default values for one or more of the workout function parameters that are not included in the given parameters and are not included in the at least one previously unspecified parameter.

55. The method of any one of examples 27-54, further comprising:
receiving further measurements indicative of power output as the adaptive training program is performed;
identifying further work values based on the further measurements indicative of power output;
updating the ability function to further fit the further work values;
updating one or more parameters of the workout function based on a comparison of the workout function to the updated ability function;
generating an updated adaptive training program based on the updated parameters; and
updating the output or automatic workout settings based on the updated adaptive training program.

56. A computer-readable storage medium storing instructions that, when executed by a computing system, cause the computing system to perform operations for automatically providing an adaptive training program, the operations comprising:
obtaining given parameters for a training session;

obtaining measurements indicative of power output;
generating the adaptive training program by:
   determining, based on the measurements indicative of power output, an ability function or critical power assessment; and
   using (A) the ability function or critical power assessment and (B) the given parameters, generating the training program including a value for at least one previously unspecified parameter; and
providing the adaptive training program.

57. The computer-readable storage medium of example 56, wherein the operations further comprise identifying a work value for each particular window size, of multiple window size durations of the measurements indicative of power output, by identifying a largest integration, of a function specified by the measurements indicative of power output, for an interval matching the particular window size.

58. The computer-readable storage medium of example 57, wherein determining the ability function or critical power assessment comprises fitting a function to the work values identified for the multiple window size durations.

59. The computer-readable storage medium of example 57, wherein generating the training program is performed by computing values for each of the at least one previously unspecified parameter, such that values of a workout function that uses the at least one previously unspecified parameter do not exceed corresponding values of the ability function for any time during a duration for the training session.

60. The computer-readable storage medium of any one of examples 56-59, wherein the measurements indicative of power output are obtained through manual entry by a user.

61. The computer-readable storage medium of any one of examples 56-59, wherein the measurements indicative of power output are obtained through recorded workout statistics taken by a wearable fitness tracker.

62. The computer-readable storage medium of any one of examples 56-59, wherein the measurements indicative of power output are obtained through an instrument system integrated into a workout apparatus.

63. The computer-readable storage medium of example 58,
   wherein the computing system is coupled to a network connecting multiple workout machines;
   wherein the measurements indicative of power output are taken by a first of the networked workout machines;
   wherein a second set of measurements indicative of power output are taken, by a second of the networked workout machines, which are transformed into additional work values for corresponding window sizes; and
   wherein the fitting the function to the work values identified for the multiple window size durations further comprises also fitting the function to the additional work values.

64. The computer-readable storage medium of example 58,
   wherein the computing system is coupled to a network connecting multiple workout machines;
   wherein the measurements indicative of power output are taken by a first of the networked workout machines;
   wherein a second set of measurements indicative of power output are taken, by a second of the networked workout machines, which are transformed into additional work values for corresponding window sizes; and
   wherein the fitting the function to the work values identified for the multiple window size durations further comprises fitting the function also to the additional work values; and
   wherein the fitting the function to the work values and to the additional work values comprises:
      selecting, for each particular window size, the largest value, of the work values and to the additional work values, corresponding to that particular window size; and
      fitting the function to the selected largest values for the window sizes.

65. The computer-readable storage medium of any one of examples 56-64, wherein the operations are performed by a server system connected to multiple workout machines.

66. The computer-readable storage medium of any one claims 56-65, wherein generating the adaptive training program is in response to an identification comprising:
   a code indicative of a user or of a workout apparatus, supplied by the user, by a mobile device associated with the user, or by the workout apparatus.

67. The computer-readable storage medium of example 66,
   wherein the generation of the adaptive training program is in response to the identification comprising the code indicative of the workout apparatus; and
   wherein the code indicative of the workout apparatus is supplied to the mobile device through an image capture system on the mobile device capturing an alphanumeric code, bar code, or QR code displayed in conjunction with the workout apparatus.

68. The computer-readable storage medium of example 66,
   wherein the generation of the adaptive training program is in response to the identification comprising the code indicative of the user; and
   wherein the code indicative of the user is supplied by communication of the code, to the workout apparatus, by the mobile device.

69. The computer-readable storage medium of any one of examples 56-64, wherein the operations are performed by a workout machine.

70. The computer-readable storage medium of any one of examples 56-64, wherein the operations are performed by a mobile device associated with a user of a workout apparatus.

71. The computer-readable storage medium of any one of examples 56-70, wherein providing the adaptive training program comprises providing output to a server system, the output comprising at least an indication of the at least one previously unspecified parameter.

72. The computer-readable storage medium of any one of examples 56-71, wherein providing the adaptive training program comprises providing output to a mobile device, the output comprising at least an indication of the at least one previously unspecified parameter.

73. The computer-readable storage medium of any one of examples 56-72, wherein providing the adaptive training program comprises providing output to a mobile device, the output comprising data to be operated on by execution of instructions on the mobile device, configured to provide a display for a user to implement the adaptive training program.

74. The computer-readable storage medium of any one of examples 56-73, wherein providing the adaptive training program comprises providing output to a workout apparatus, the output configured to cause a display of the workout apparatus to provide instructions for the adaptive training program.

75. The computer-readable storage medium of any one of examples 56-74, wherein providing the adaptive training program comprises providing automatic workout settings to a workout apparatus, wherein the workout apparatus automatically implements the adaptive training program based on the automatic workout settings.

76. The computer-readable storage medium of any one of examples 56-75, wherein the operations further comprise providing output to a server system or a mobile device, the output being stored in association with a user profile comprising one or more of:
   at least some of the identified work values;
   the ability function;
   statistics of the adaptive training program;
   measures of actual performance during the training session;
   biographic specifics; or
   any combination thereof.

77. The computer-readable storage medium of any one of examples 56-76, wherein the operations further comprise providing an internet-based interface, accessible through a web browser or mobile device application, wherein the internet-based interface provides access to a user profile associated with multiple workouts performed by a user.

78. The computer-readable storage medium of any of any one of examples 56-77, wherein the measurements indicative of power output comprise one or more of:
   speed;
   revolutions-per-minute;
   resistance;
   incline;
   distance and duration;
   weight and repetitions; or
   any combination thereof.

79. The computer-readable storage medium of any one of examples 56-78 wherein the ability function is a linear function.

80. The computer-readable storage medium of any one of examples 56-79,
   wherein the operations further comprise computing the value for the at least one previously unspecified parameter by:
      obtaining a workout function, from a set of pre-defined functions, based on an indicated workout type for the adaptive training program;
      filling the given parameters into the workout function; and
      solving for the at least one previously unspecified parameter, wherein the at least one previously unspecified parameter includes exactly one parameter; and
   wherein generating the adaptive training program comprises:
      selecting data to display instructing a user to perform a workout based on at least the at least one previously unspecified parameter; or
      specifying automatic workout settings based on the at least one previously unspecified parameter.

81. The computer-readable storage medium of example 53, wherein filling in the one or more given parameters in the pre-defined function comprises using one or more default values for one or more of the workout function parameters that are not included in the given parameters and are not included in the at least one previously unspecified parameter.

82. The computer-readable storage medium of any one of examples 56-81, wherein the operations further comprise:
   receiving further measurements indicative of power output as the adaptive training program is performed;
   identifying further work values based on the further measurements indicative of power output;
   updating the ability function to further fit the further work values; and
   generating an updated adaptive training program based on the ability function.

83. A method performed by a mobile device for providing an adaptive training program, the method comprising:
   obtaining measurements indicative of power output;
      identifying a work value for each particular window size, of multiple window size durations of the measurements indicative of power output, by:
         identifying a largest integration, of a function specified by the measurements indicative of power output, for an interval matching the particular window size;
   fitting, as an ability function, a function to the work values identified for the multiple window size durations;
   computing a value for at least one previously unspecified parameter for a training session, such that values of a workout function, that uses the previously unspecified parameter, do not exceed corresponding values of the ability function for any time during a duration for the training session;
   using the at least one previously unspecified parameter to generate the adaptive training program; and
   transmitting automatic workout settings based on the adaptive training program to a workout apparatus, wherein the workout apparatus automatically implements the adaptive training program based on the automatic workout settings.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Reference in this specification to "implementations" (e.g. "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle specified number of items, or that an item under comparison has a value within a middle specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

I claim:

1. A computer-readable storage medium storing instructions that, when executed by a computing system, cause the computing system to perform operations for automatically providing a user-specific training program, the operations comprising:
    obtaining multiple power output functions, wherein at least two of the multiple power functions are based on activities of a user performed on different dates;
    determining an ability function for the user, by:
        computing work values, wherein each work value is an integration of one of the multiple power functions for an interval that is of a particular size, and is selected as being the largest integration result across all of the multiple power output functions for the interval size; and
        determining the ability function as a function fit to the computed work values;
    obtaining indications of work for a training session;
    generating the user-specific training program by adjusting a workout function based on (A) the ability function and (B) the indications of work for the training session; and
    providing the user-specific training program.

2. The computer-readable storage medium of claim 1, wherein the work values are weighted based on the date the corresponding power output function was performed.

3. The computer-readable storage medium of claim 1, wherein computing each work value corresponding to a particular interval size for each particular power output function, of the multiple power output functions, comprises determining a largest integration of the particular power output function, over the particular interval size.

4. The computer-readable storage medium of claim 3, wherein computing the work value, corresponding to a particular interval size for one of the particular power output functions, further comprises:
    identifying that the determined largest integration of the one of the particular power output functions, over the particular interval size, exceeds a previously stored work value for the particular interval size; and
    in response, replacing a stored work value for the particular interval size with the determined largest integration of the one of the particular power output functions.

5. The computer-readable storage medium of claim 1, wherein the activities performed on different dates are performed on at least two different workout apparatus connected via a network.

6. The computer-readable storage medium of claim 1, wherein generating the user-specific training program comprises adjusting a workout function such that no value of the workout function exceeds a value of the ability function during a duration set for a training session.

7. The computer-readable storage medium of claim 1, wherein the multiple power output functions are associated with each other in response to receiving an identification comprising one or more codes, each code indicative of a workout apparatus or of the user, received via a mobile device associated with the user or with one or more workout apparatus on which the activities performed on different dates are performed.

8. The computer-readable storage medium of claim 1, wherein providing the user-specific training program causes a workout apparatus to display features of the user-specific training program as user instructions.

9. The computer-readable storage medium of claim 1, wherein providing the user-specific training program comprises automatically configuring, according to the user-specific training program, settings of a second workout apparatus that control required user power output.

10. A method for automatically providing a user-specific training program, the method comprising:
    obtaining multiple power output functions, wherein at least two of the multiple power functions are based on activities of a user performed on different dates;
    determining an ability function for the user, by:
        computing work values, wherein each work value is an integration of one of the multiple power functions for an interval that is of a particular size, and is selected as being the largest integration result across all of the multiple power output functions for the interval size; and determining the ability function as a function fit to the computed work values;

obtaining indications of work for a training session;

generating the user-specific training program by adjusting a workout function based on (A) the ability function and (B) the indications of work for the training session; and providing the user-specific training program.

11. The method of claim 10, wherein the work values are weighted based on the date the corresponding power output function was performed.

12. The method of claim 10, wherein computing each work value corresponding to a particular interval size for each particular power output function, of the multiple power output functions, comprises determining a largest integration of the particular power output function, over the particular interval size.

13. The method of claim 12, wherein computing the work value, corresponding to a particular interval size for one of the particular power output functions, further comprises:

identifying that the determined largest integration of the one of the particular power output functions, over the particular interval size, exceeds a previously stored work value for the particular interval size; and in response, replacing a stored work value for the particular interval size with the determined largest integration of the one of the particular power output functions.

14. The method of claim 10, wherein the activities performed on different dates are performed on at least two different workout apparatus connected via a network.

15. The method of claim 10, wherein generating the user-specific training program comprises adjusting a workout function such that no value of the workout function exceeds a value of the ability function during a duration set for a training session.

16. The method of claim 10, wherein providing the user-specific training program comprises automatically configuring, according to the user-specific training program, settings of a second workout apparatus that control required user power output.

17. A computing system for automatically providing a user-specific training program, the computing system comprising:

one or more processors; and one or more memories storing instructions that, when executed by the one or more processors, cause the computing system to perform operations comprising:

obtaining indications of power output of a user;

determining an ability function or critical power assessment, wherein the ability function or critical power assessment provides work values specific to the user based on integrations of intervals of the indications of power output;

obtaining indications of work for a training session;

generating the user-specific training program by adjusting a workout function based on (A) the ability function or critical power assessment and (B) the indications of work for the training session; and providing the user-specific training program.

18. The computing system of claim 17, wherein the indications of power output are a power function and wherein determining the ability function or critical power assessment comprises deterring the ability function by:

computing work values, wherein each work value is an integration of the power function, for an interval that is of a particular size, that produces the largest integration result across the power function; and determining the ability function as a function fit to the computed work values.

19. The computing system of claim 17, wherein determining the ability function or critical power assessment comprises deterring the ability function; and wherein adjusting the workout function comprises adjusting the workout function such that no value of the workout function exceeds a value of the ability function for any given value for a duration of a training session.

20. The computing system of claim 17, wherein providing the user-specific training program comprises automatically configuring, according to the user-specific training program, settings of a workout apparatus that control required user power output.

* * * * *